(12) United States Patent
Mogul

(10) Patent No.: US 7,269,453 B2
(45) Date of Patent: Sep. 11, 2007

(54) STEERABLE DIAGNOSTIC CATHETERS

(76) Inventor: Jamil Mogul, 2665 Somerset Park Cir., San Jose, CA (US) 95132

( * ) Notice: Subject to any disclaimer, the term of this patent is extended or adjusted under 35 U.S.C. 154(b) by 0 days.

(21) Appl. No.: 10/816,821

(22) Filed: Apr. 5, 2004

(65) Prior Publication Data
US 2004/0193032 A1   Sep. 30, 2004

Related U.S. Application Data

(60) Division of application No. 10/099,576, filed on Mar. 14, 2002, now Pat. No. 6,829,497, which is a continuation-in-part of application No. 09/399,929, filed on Sep. 21, 1999, now abandoned.

(51) Int. Cl.
*A61B 5/042* (2006.01)
(52) U.S. Cl. .................. 600/374; 604/528; 607/122
(58) Field of Classification Search .............. 600/373, 600/374; 606/41, 46; 607/119, 122; 604/528
See application file for complete search history.

(56) References Cited

U.S. PATENT DOCUMENTS

| | | | | |
|---|---|---|---|---|
| 4,444,195 A | * | 4/1984 | Gold | 600/374 |
| 5,462,527 A | * | 10/1995 | Stevens-Wright et al. | 604/528 |
| 5,487,757 A | * | 1/1996 | Truckai et al. | 604/264 |
| 5,531,686 A | * | 7/1996 | Lundquist et al. | 604/95.04 |
| 6,071,282 A | * | 6/2000 | Fleischman | 606/41 |
| 6,741,878 B2 | * | 5/2004 | Fuimaono et al. | 600/374 |

* cited by examiner

*Primary Examiner*—Lee S. Cohen
(74) *Attorney, Agent, or Firm*—Buchanan Ingersoll & Rooney

(57) ABSTRACT

A diagnostic catheter with a steering device to direct the distal end of the catheter while it is inserted in a vessel. The catheter may include either a bi-directional steering mechanism, or a unidirectional steering mechanism. Pre-formed catheters with no steering means are also provided. The catheter bodies include a plurality of ring electrodes used for sensing the intracardial electrogram signal during operation of the catheter. The ring electrodes are placed in ohmic contact with their corresponding signal wires by a solderless connection. In addition, the catheter may be embodied as a basket catheter including a plurality of splines. After the catheter is inserted into the vessel or organ to be examined (typically the heart), the splines may be expanded from an at-rest position to form the basket. A central retractable and steerable member is included to provide the expansion force. The expansion force can also be provided by moving the proximal portion of the catheter relative to the central member. Each of the splines forming the basket includes a length of spring wire disposed therein to provide conformal forces causing the splines to conform to the surfaces being inspected.

13 Claims, 31 Drawing Sheets

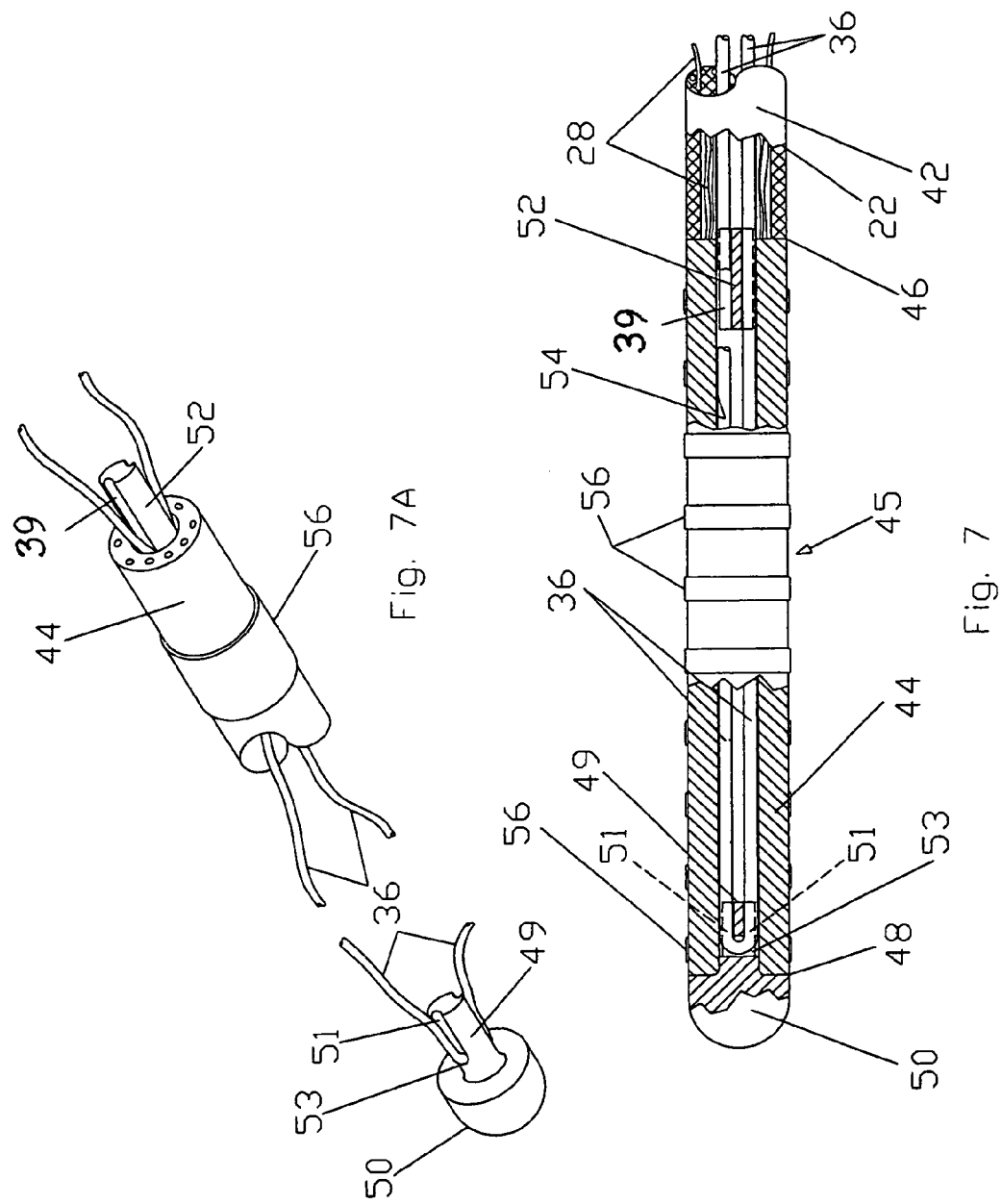

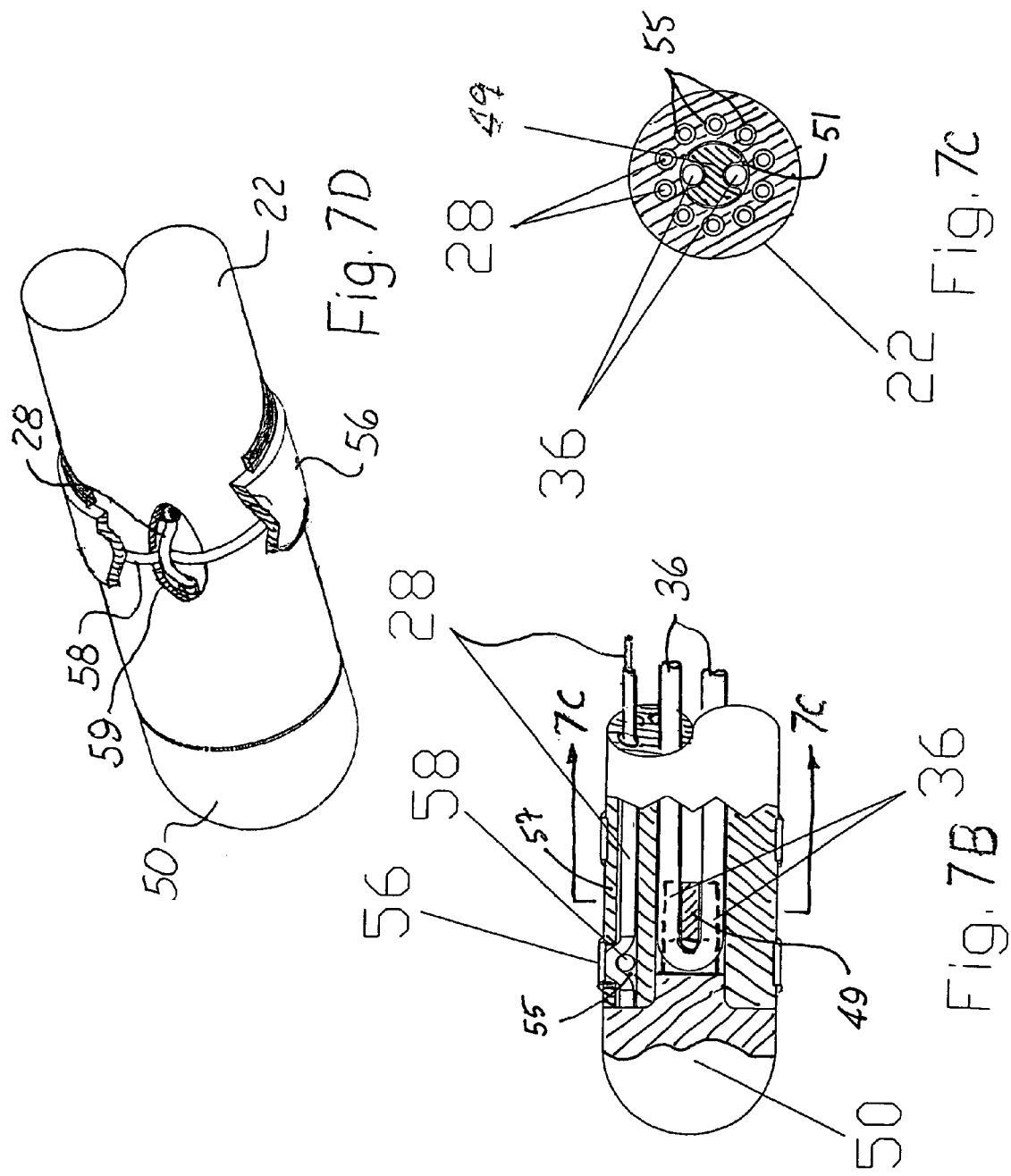

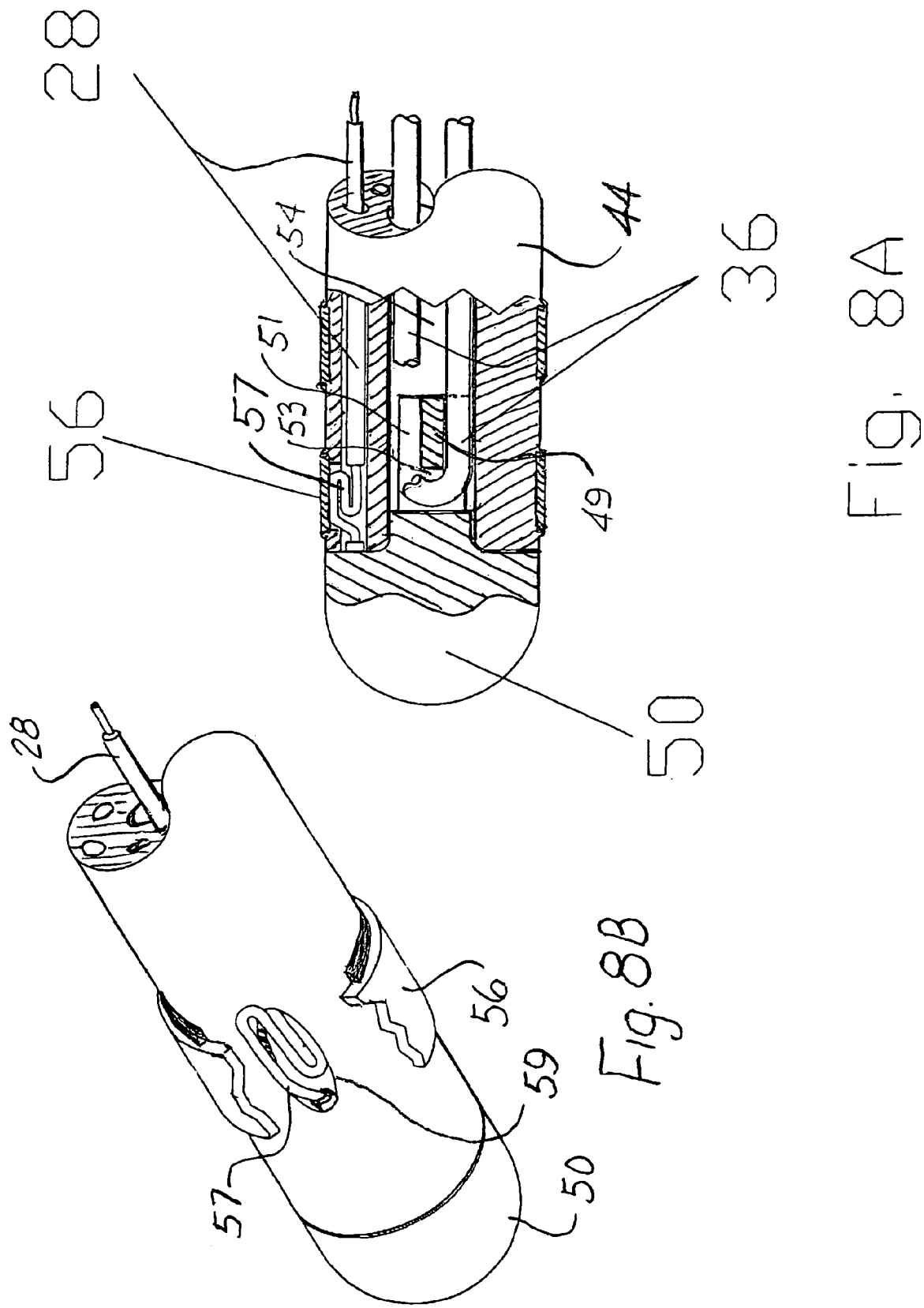

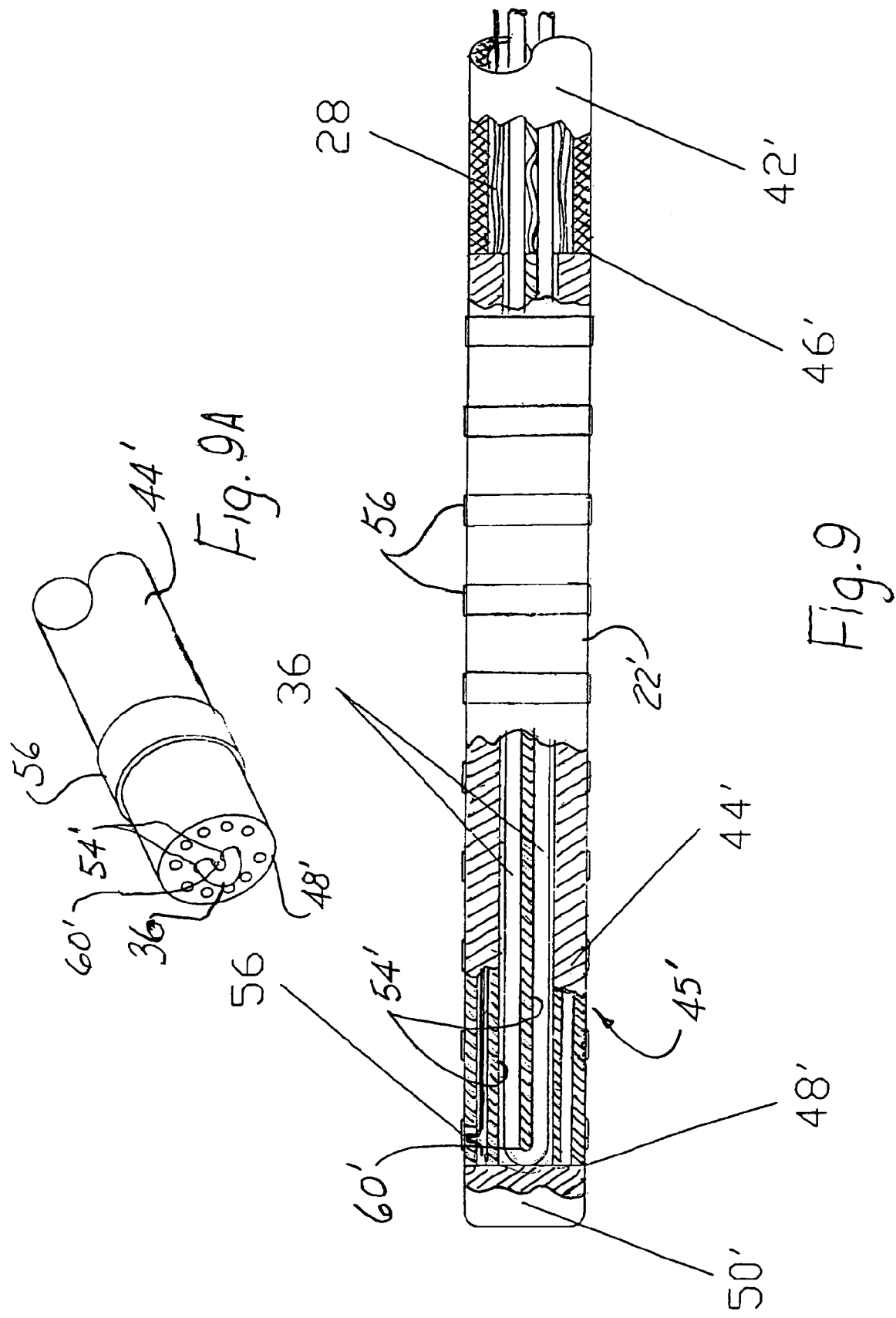

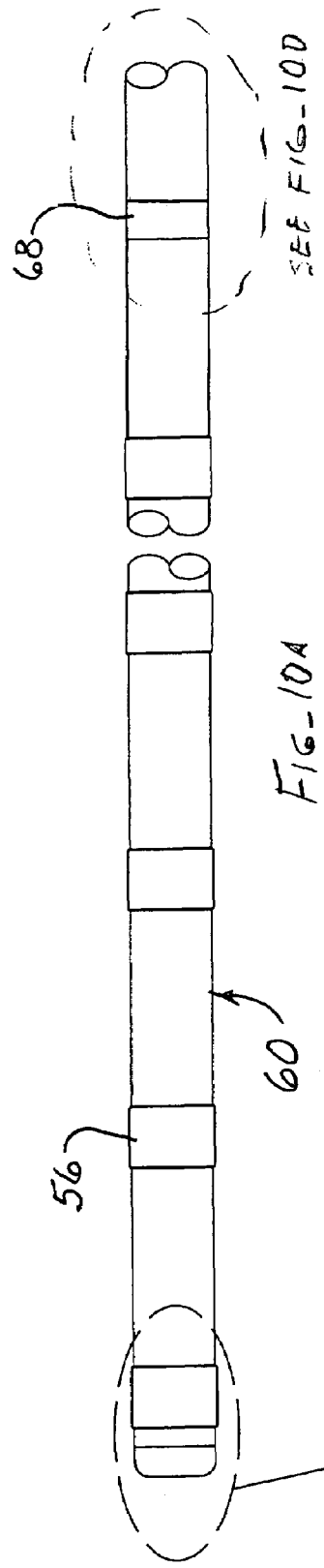
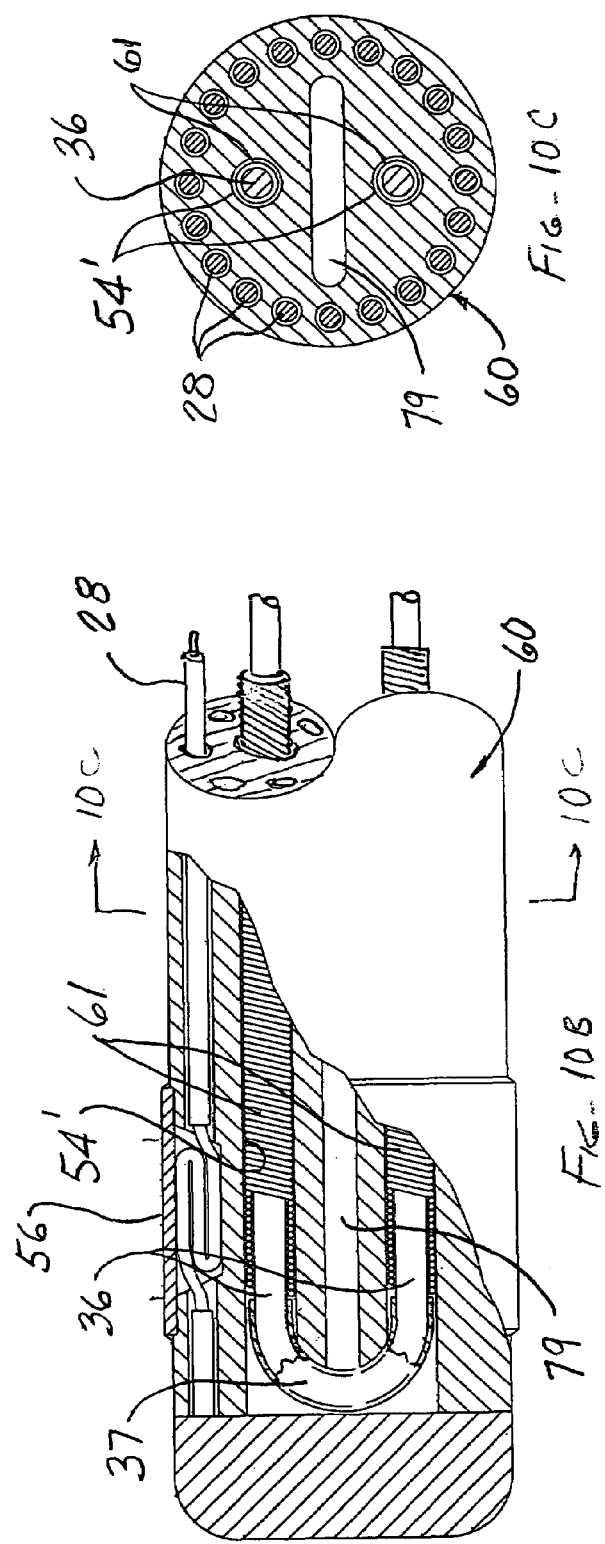

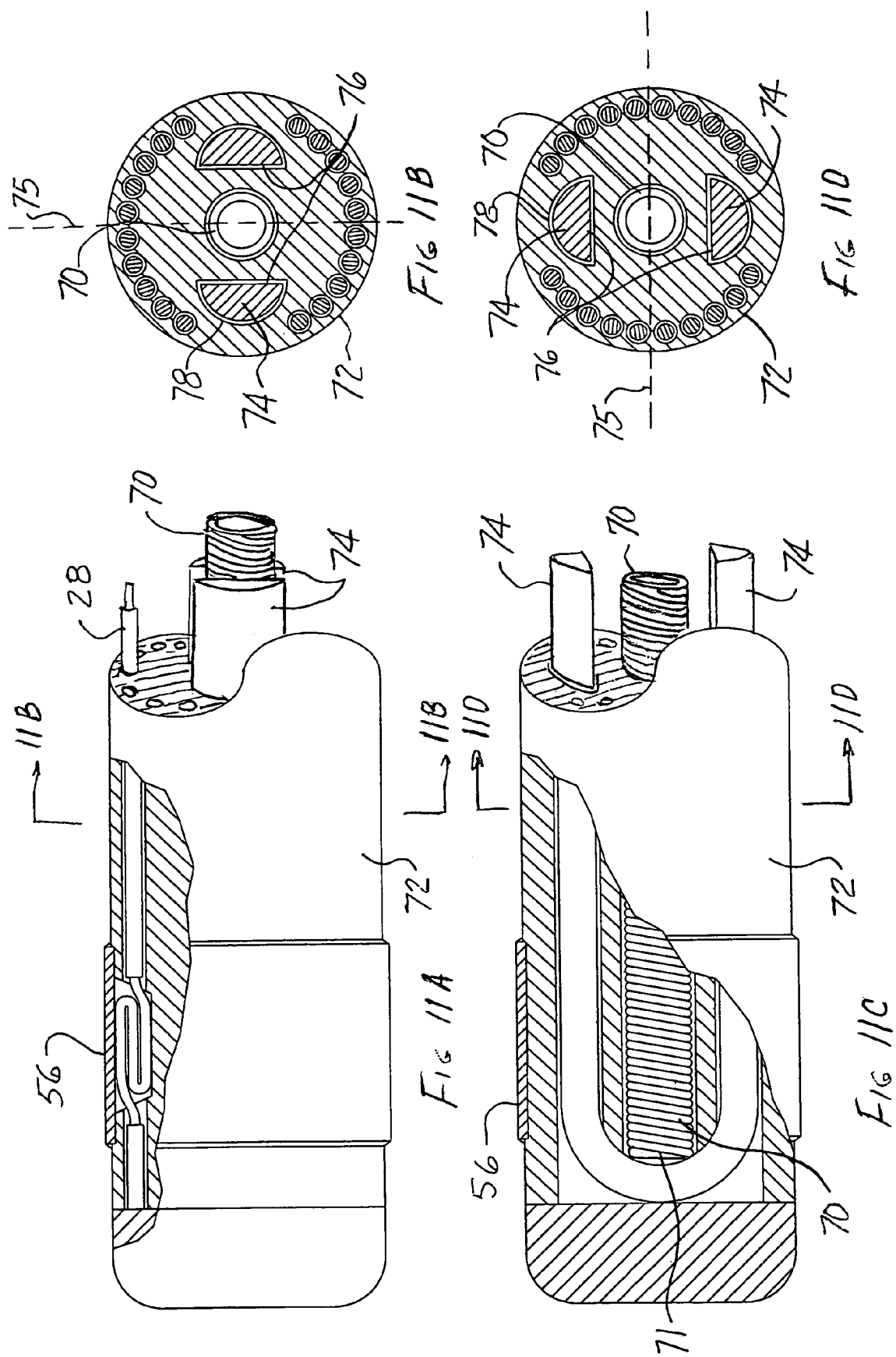

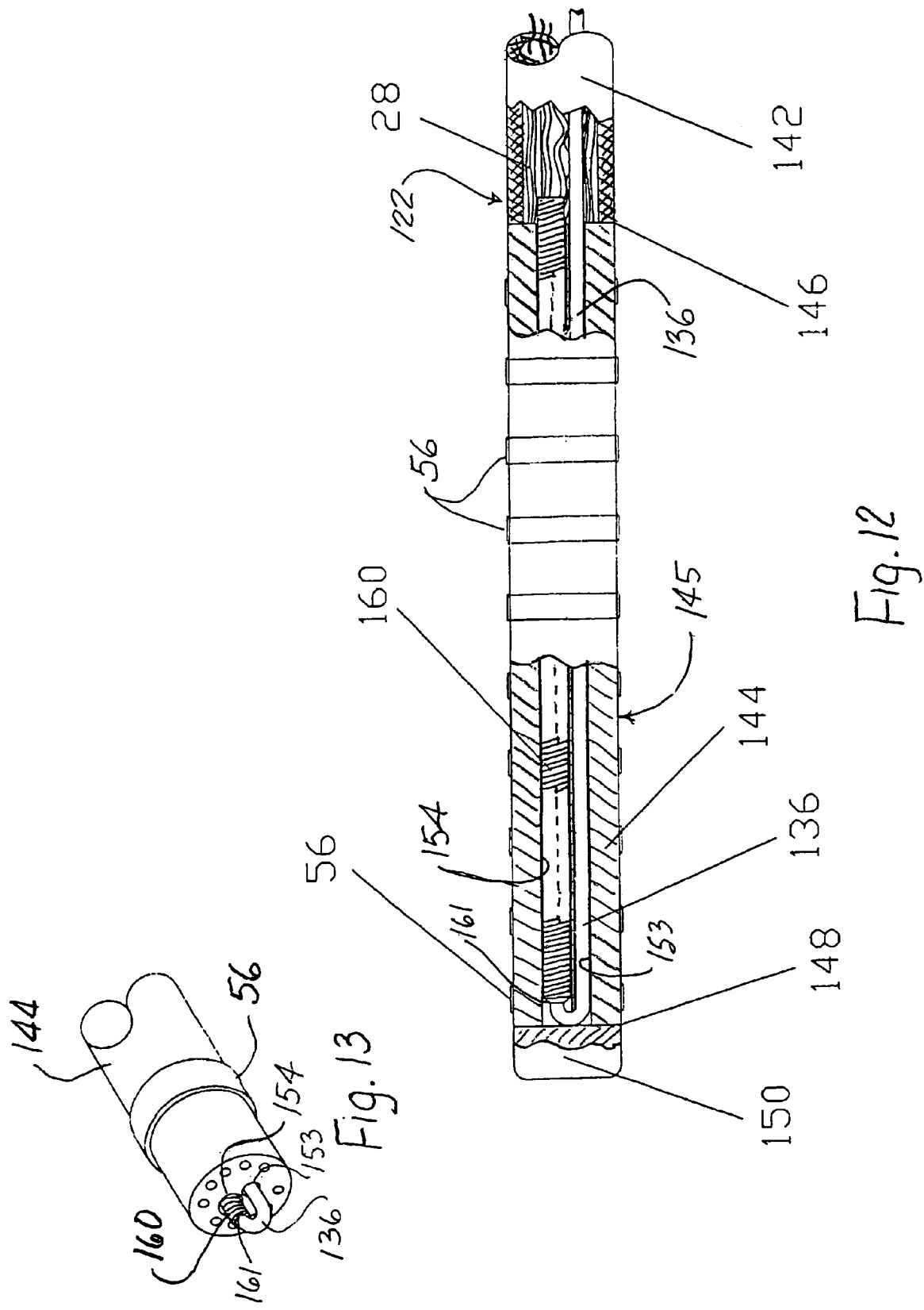

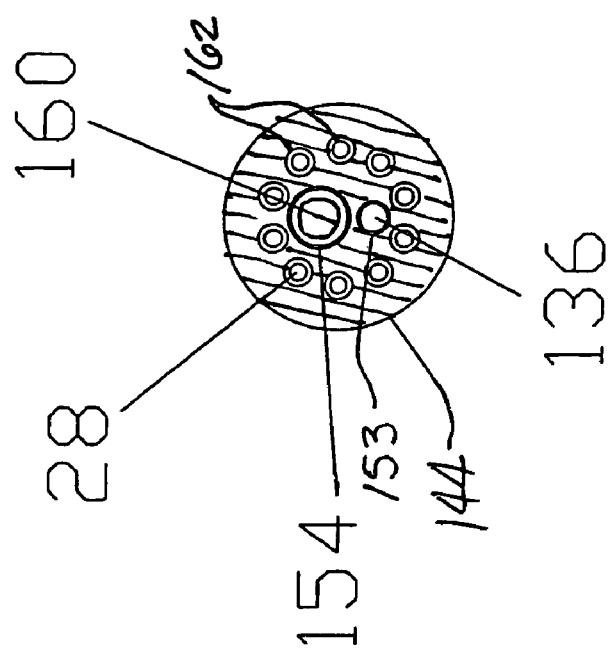
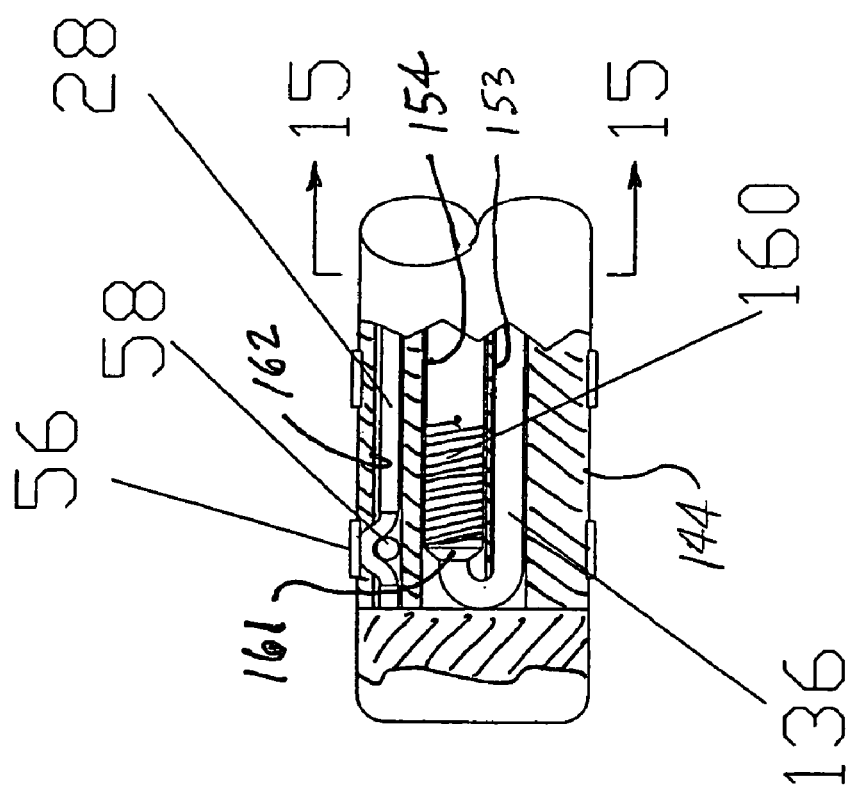
Fig. 15
Fig. 14

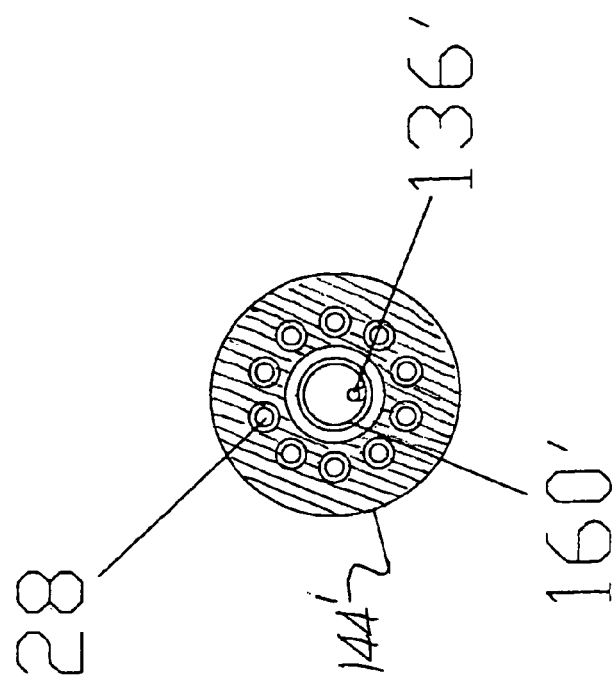
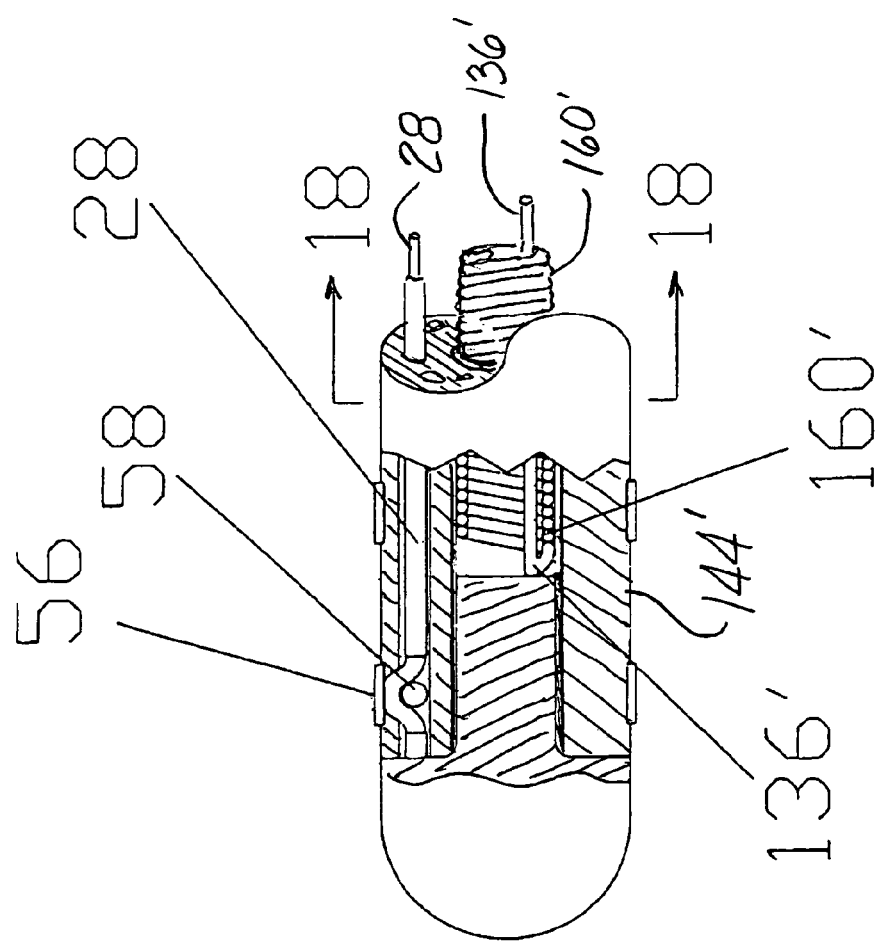

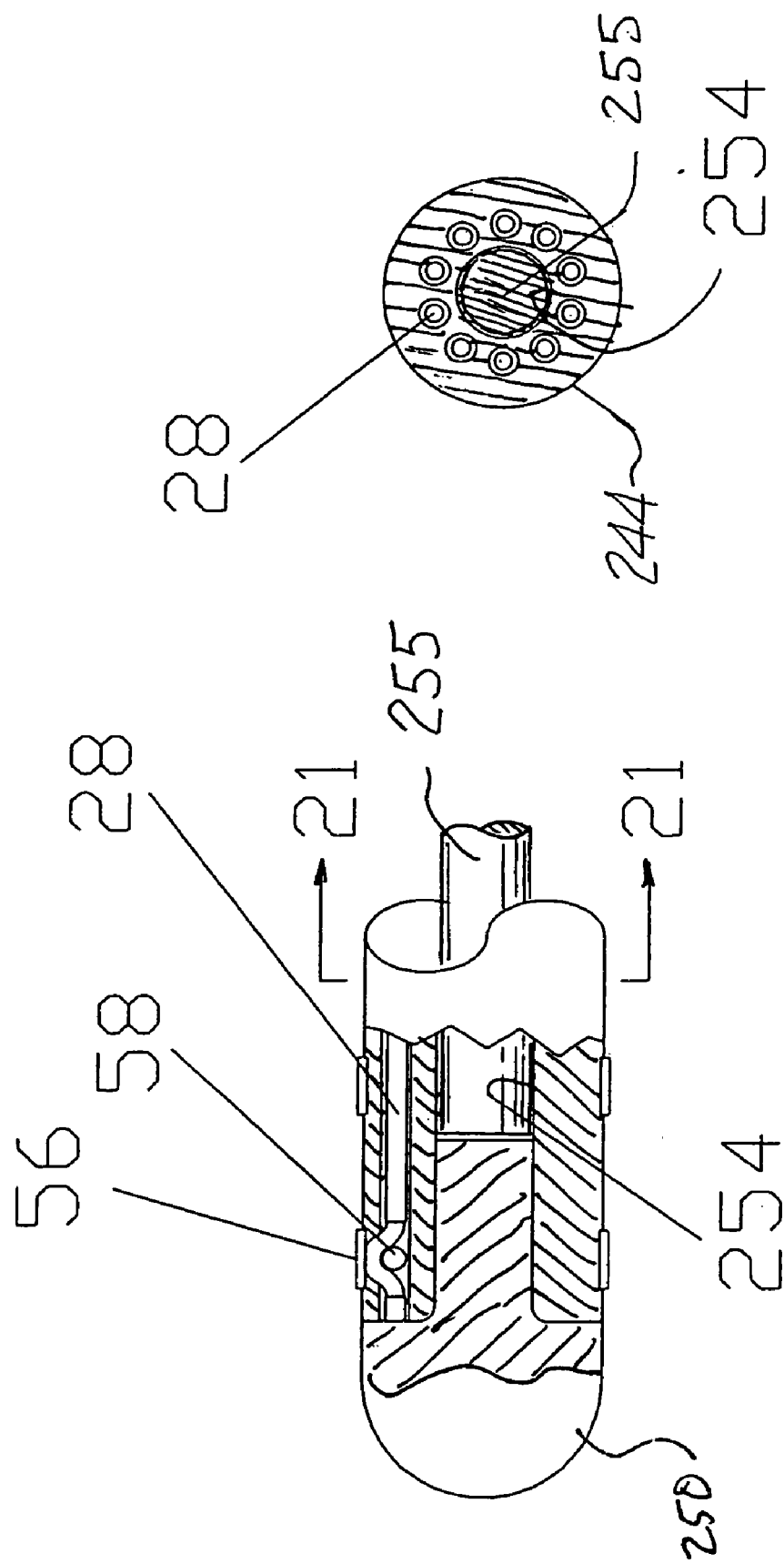

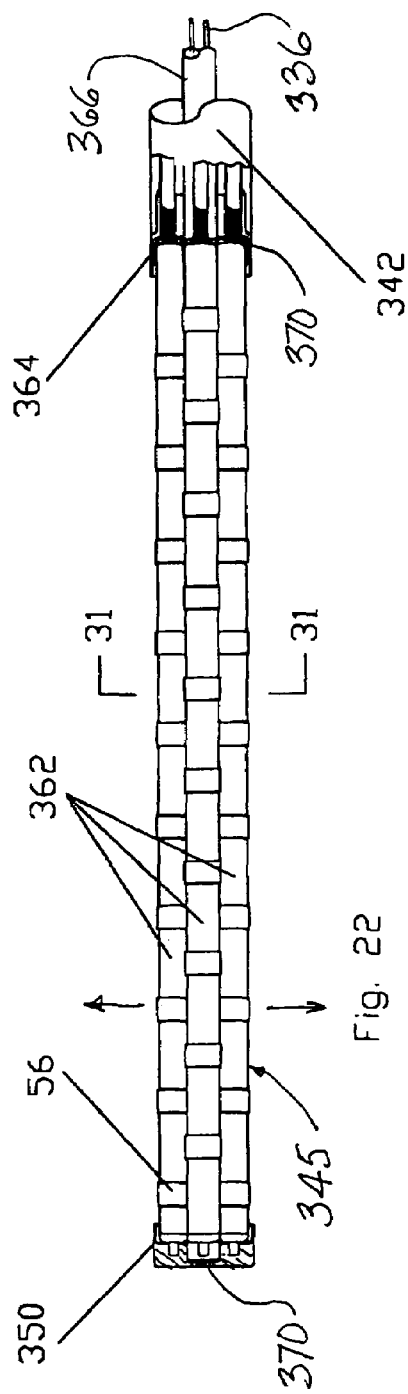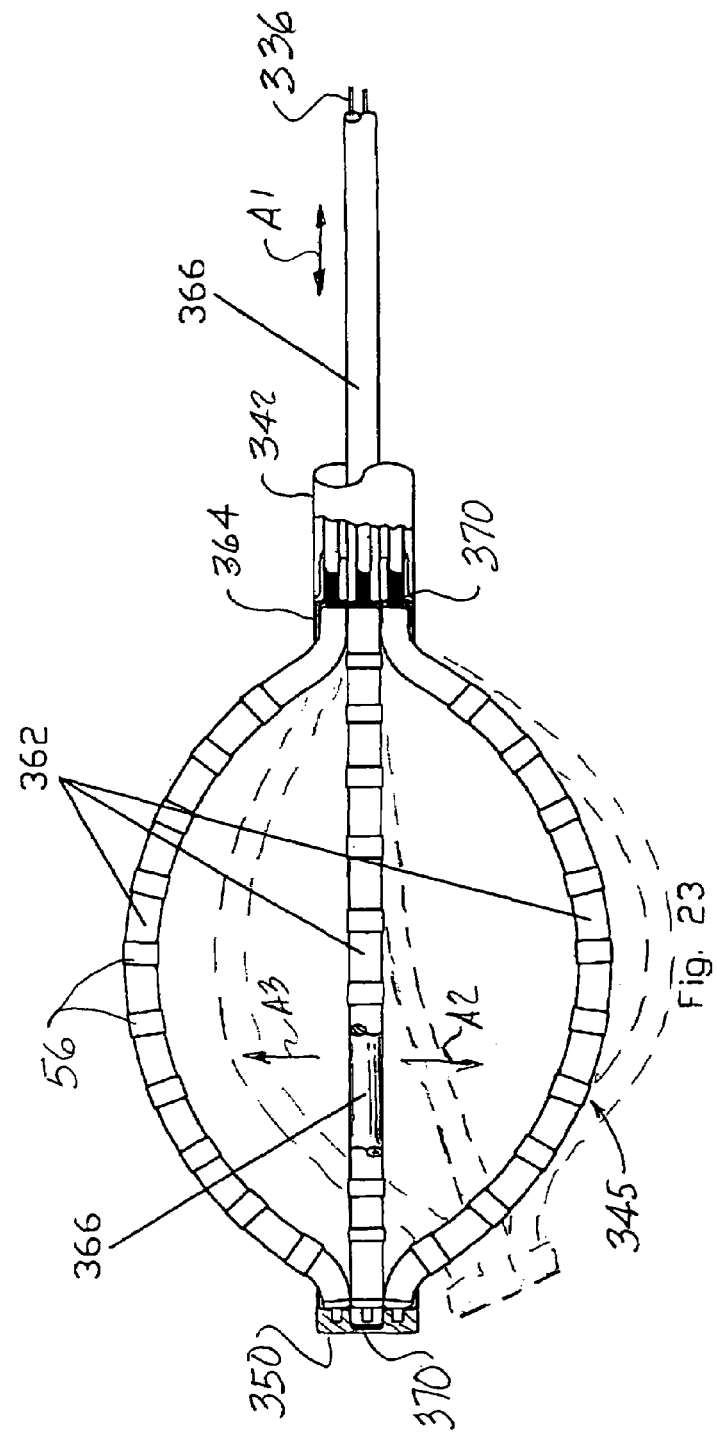

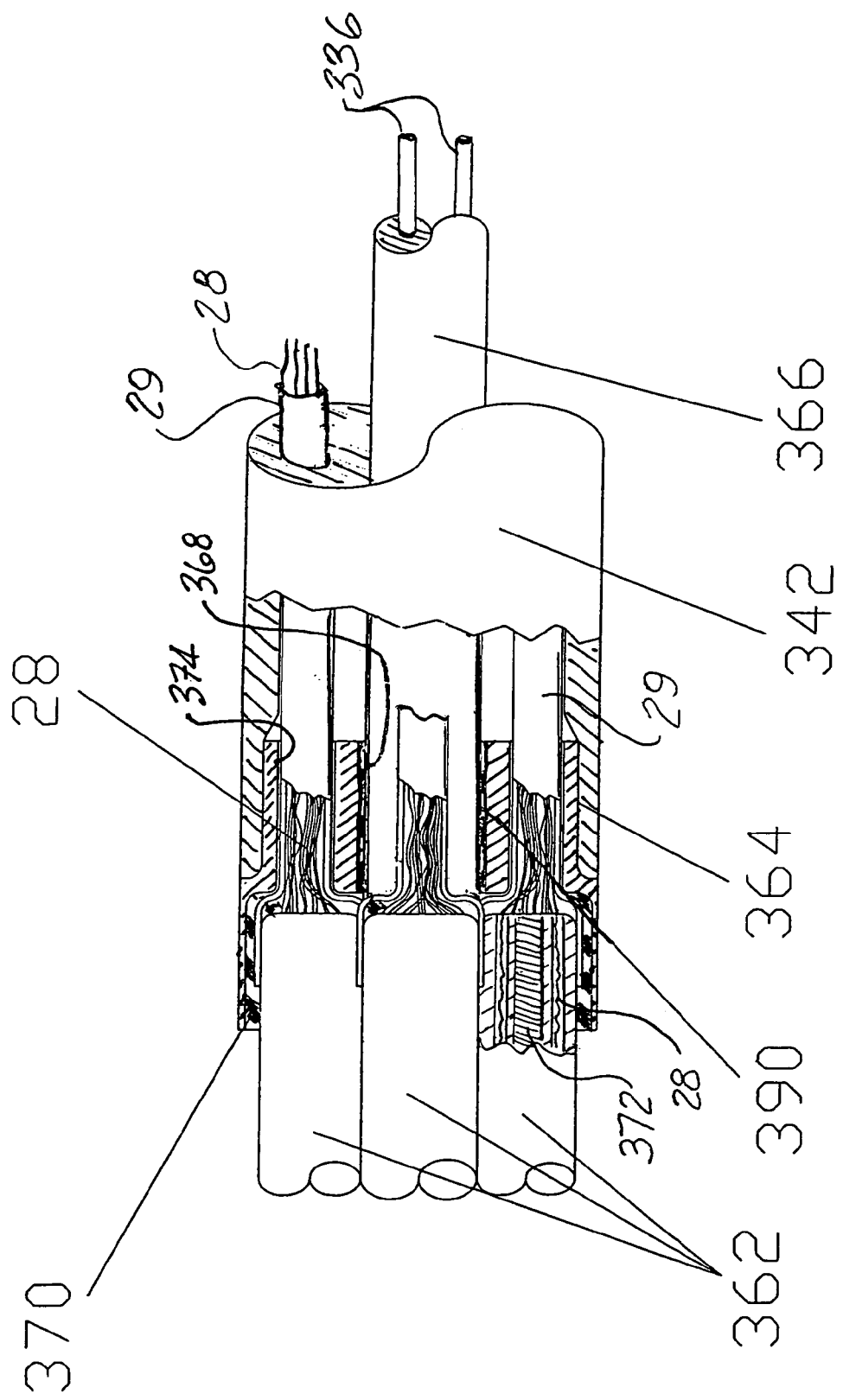

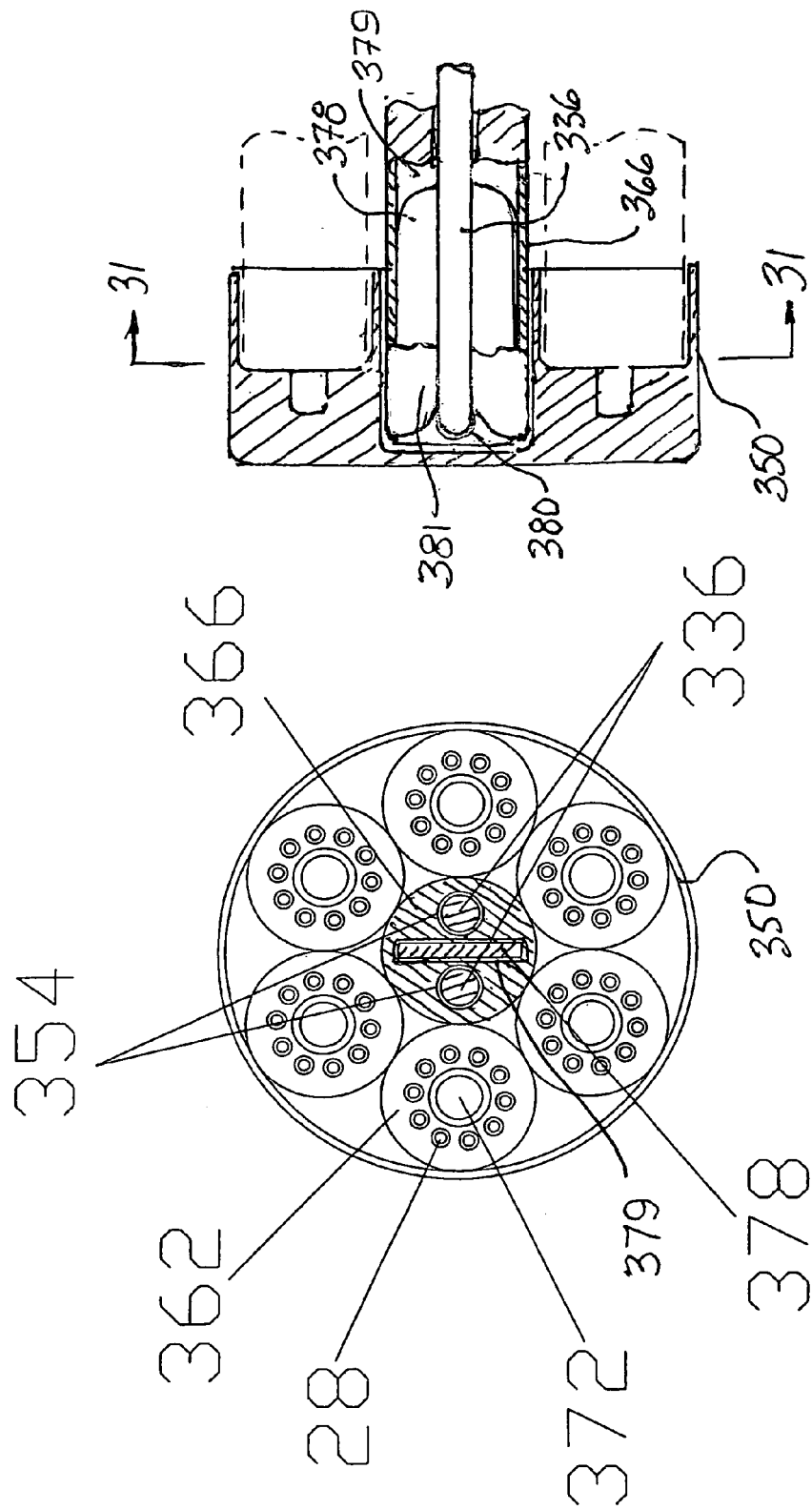

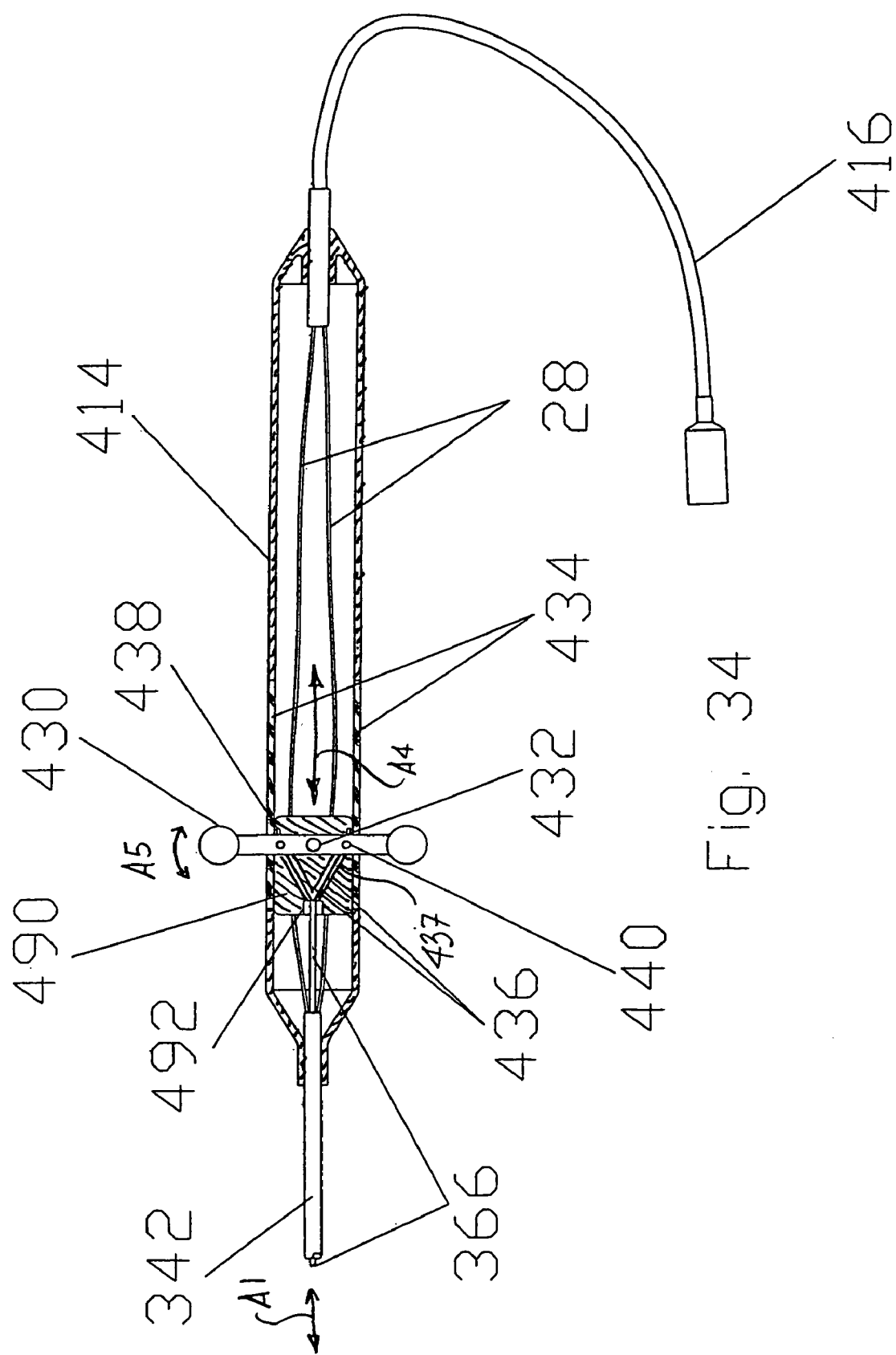

STEERABLE DIAGNOSTIC CATHETERS

CROSS REFERENCE TO RELATED APPLICATIONS

This application is a divisional of U.S. patent application Ser. No. 10/099,576 which was filed on Mar. 14, 2002 now U.S. Pat. No. 6,829,497, which is a continuation-in-part of U.S. patent application Ser. No. 09/399,929, filed Sep. 21, 1999, now abandoned, the specifications and drawings of which are incorporated herein by reference.

FIELD OF THE INVENTION

The present invention relates generally to medical diagnostic equipment, and more particularly is a new construction for steerable diagnostic catheters.

BACKGROUND OF THE INVENTION

Heart disease is one of the leading causes of death in the world. Heart disease is found in all countries and across all ages, socioeconomic levels, occupations, and sexes. Because heart disease is so universally common, the diagnosis and treatment of heart disease is an immensely important field.

One of the chief difficulties in examining the heart is that, as with all internal organs, the defects cannot be readily seen. It is therefore necessary to use some instrument that enables the user to "see" inside the organ. One of the processes that enables physicians in the treatment of hear disease is an electrophysiological examination. This examination requires the use of a catheter with a plurality of ring electrodes on a distal end. In addition to the ring electrodes, the catheter may also carry one or more probes at its distal tip.

The catheter is introduced through the patient's veins or arteries into the areas of the heart, or the associated blood vessels, which require analysis. Due to the many available probes and testing devices, it is not uncommon for the examining physician to have several catheters in use at a given time in a single patient's heart. When this is the case, the catheter entry path becomes very congested. Due to the relatively large size of existing diagnostic catheters, it is sometimes necessary to remove one catheter and replace it with another during a procedure. In addition to the distinct possibility of dislodging the already positioned catheters, the removal of a catheter can itself damage the organ if the catheter is removed improperly or becomes entangled with another catheter.

Another of the shortcomings in the prior art catheter devices is that they are very difficult to position correctly in the vessel or organ being examined. There are only very limited means of guiding the catheter. Smaller existing art catheters are generally provided with a fixed curvature at the distal end.

Another problem inherent in the prior art devices is that the shape of the probes on the distal ends of the catheters is fixed. This contributes to the problem of congestion in the entry path, as a different catheter must be introduced when the physician wishes to examine different vessel and organ wall shapes and sizes. When a basket catheter is being used, a sheath must be placed over the multiple probes or basket to introduce the catheter into the vessel.

Accordingly, it is an object of the present invention to provide an electrophysiology catheter that comprises a means to steer the distal end while providing a main body that is more narrow than those of current art devices.

It is a further object of the present invention to provide a catheter which allows the size, shape, and direction of travel of a probe to be changed while in the vessel or organ. This innovation is particularly applicable to basket catheters.

SUMMARY OF THE INVENTION

The present invention is a diagnostic catheter with a steering means to direct the distal end of the catheter while it is inserted in a vessel. The device may include either a bi-directional steering mechanism, or a unidirectional steering mechanism. Pre-formed catheters with no steering means are also provided.

The catheter bodies include a plurality of ring electrodes used for sensing the intracardial electrogram signal during operation of the catheter. The ring electrodes are placed in ohmic contact with their corresponding signal wires by a solderless connection.

In addition, the catheter may be embodied as a basket catheter. The basket catheter includes a plurality of splines. After the catheter is inserted into the vessel or organ to be examined (typically the heart), the splines expand from an at-rest position to form the basket.

A central retractable and steerable member is included to provide the expansion force. The expansion force can be provided by moving the proximal portion of the catheter relative to the central member. Each of the splines forming the basket includes a spring wire therein to provide the compliance for the splines to be in contact with the organ while they are in the expanded position.

An advantage of the present invention is that although it is smaller in size than most current art devices, it can be steered in the vessel or organ being examined.

Another advantage of the present invention is that it has a large plurality of non-welded ring electrodes for sensing, even though the catheter is smaller in size than most current art devices.

A still further advantage of the present invention is that the distal end of the fixed shape of the catheter can be formed and fixed in any shape desired by the user.

Another advantage of the present invention is that when it is used as a basket catheter, the basket size and shape can be modified while the catheter is in use.

Yet another advantage of the present invention is that when the basket catheter version is in use, the basket can be steered in either expanded or collapsed state within the vessel or organ being examined.

Still another advantage of the present invention when it is used as a basket catheter is that no sheath is necessary for insertion of the catheter into the vessel or organ.

These and other objects and advantages of the present invention will become apparent to those skilled in the art in view of the description of the best presently known mode of carrying out the invention ad described herein and as illustrated in the drawings.

BRIEF DESCRIPTION OF THE DRAWINGS

FIG. 7 is a partially broken side view of a bi-directional steerable catheter.

FIG. 7A is a broken perspective view showing details of the embodiment of FIG. 7.

FIG. 7B is a magnified partial sectional view of the distal end of the bi-directional steerable catheter of FIG. 7.

FIG. 7C is a cross section taken along the line 7C-7C of FIG. 7B.

FIG. 7D is a broken perspective view showing the electrode connection detail of FIG. 7B.

FIG. 8A is a magnified view of the distal end of the catheter showing an alternative method for connecting the ring electrode to the signal wire.

FIG. 8B is a broken perspective view further illustrating the detail of FIG. 8A.

FIG. 9 is a broken sectional view of a second embodiment of a bi-directional steerable catheter.

FIG. 9A is a perspective view further illustrating exterior details of FIG. 9.

FIGS. 10A-10D illustrate details of another alternative embodiment of the invention.

FIGS. 11A-11D illustrate still another alternative embodiment of the invention.

FIG. 12 is a cross sectional view showing a unidirectional steerable catheter.

FIGS. 13-15 are views further illustrating details of the embodiment of FIG. 12.

FIG. 17 is a magnified sectional view of the distal end of the second embodiment of the unidirectional steerable catheter.

FIG. 18 is a cross section taken along line 18-18 in FIG. 17.

FIG. 20 is a magnified sectional view of the distal end of the fixed-shape distal end catheter.

FIG. 21 is a cross section taken along line 21-21 in FIG. 20.

FIG. 22 is a partially broken side view of a basket catheter according to the present invention.

FIG. 23 is a partially broken side view of the basket catheter of FIG. 22 after it has been inserted and shaped.

FIG. 27 shows the transition area near the proximal end of the basket catheter of FIG. 22.

FIG. 30A is a partially broken cross sectional view further illustrating the steering wire anchor means of FIG. 30 installed in a receiving slot.

FIG. 31 is a cross sectional view of the basket catheter taken along line 31-31 in FIG. 30A.

FIG. 34 is a cross sectional view of a handle for a retractable and steerable basket catheter.

DETAILED DESCRIPTION OF THE INVENTION

Figure 1:
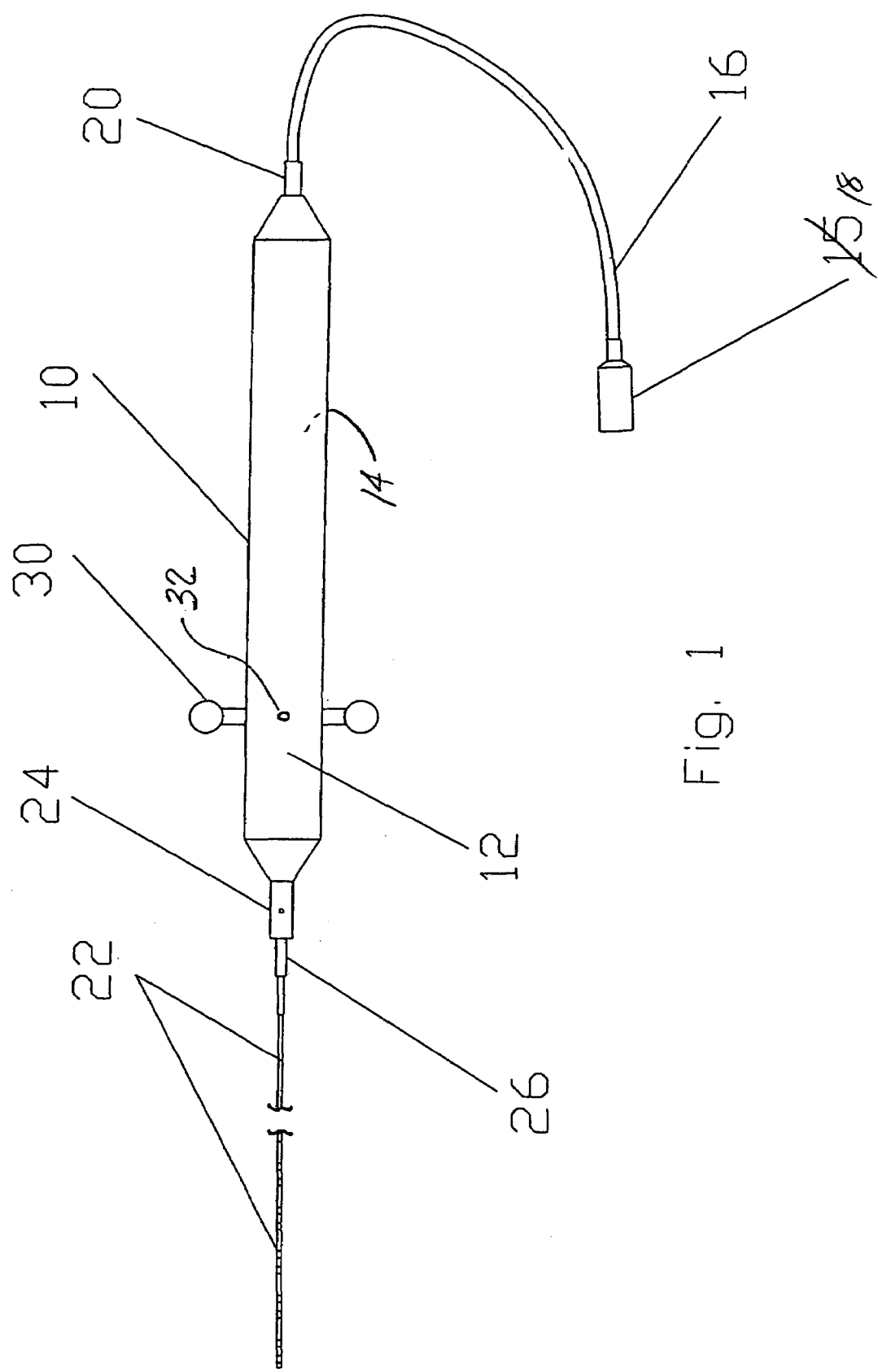
FIG. 1 is a side view of a catheter handle with a bi-directional steering mechanism.
Figure 1A:
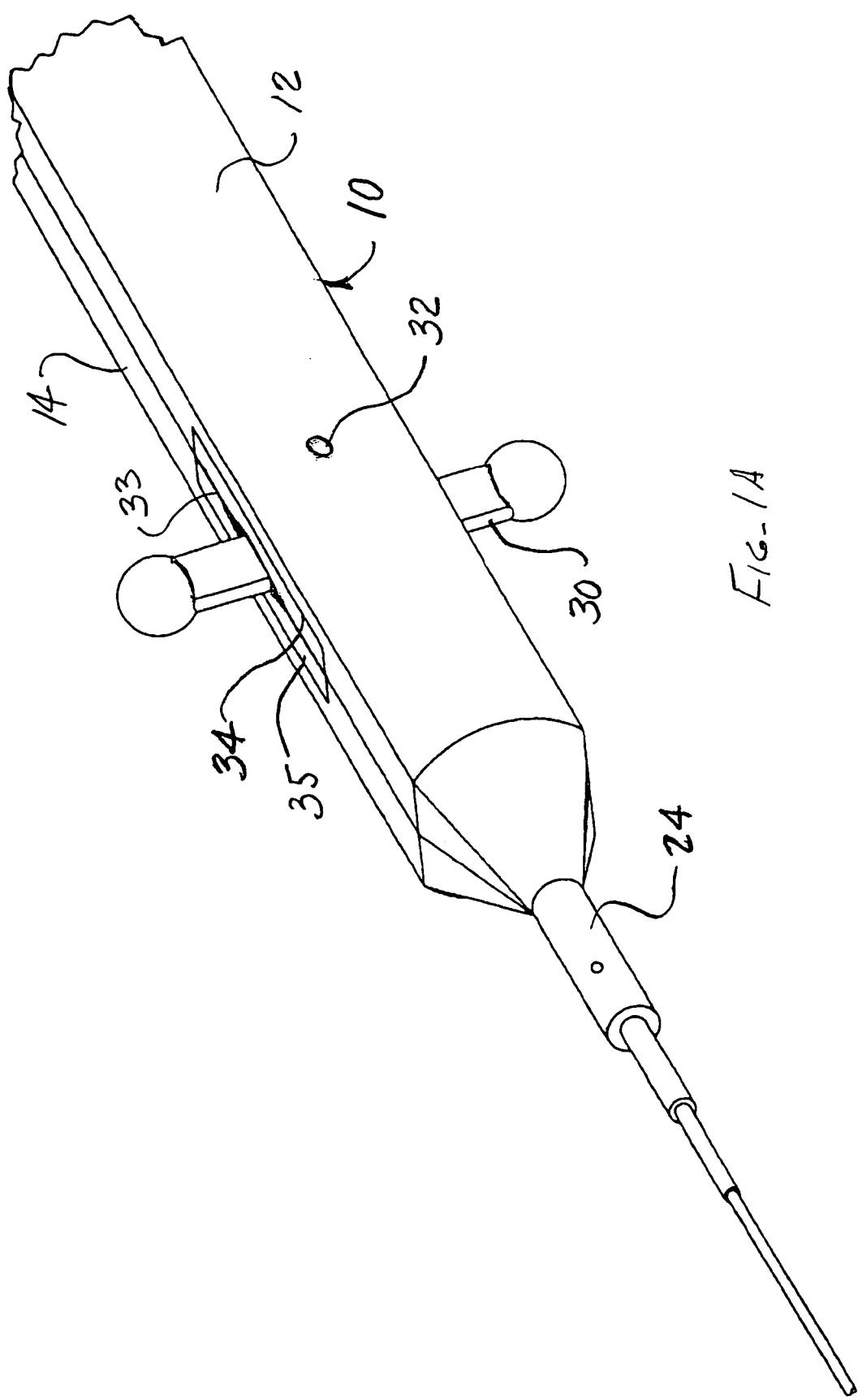
FIG. 1A is a perspective view of the catheter handle of FIG. 1.
Figure 2:
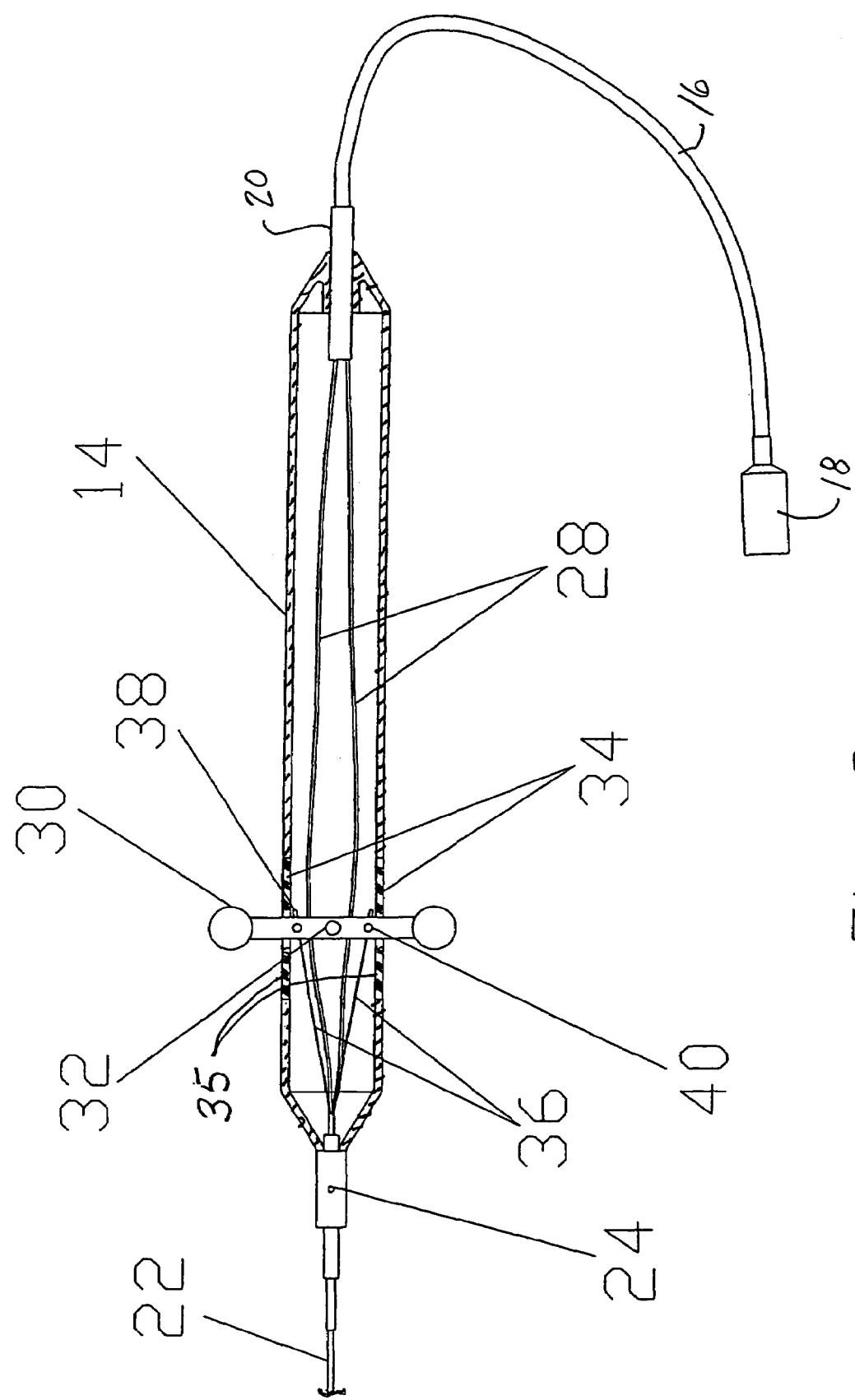
FIG. 2 is a sectional view of the catheter handle of FIG. 1.

The present invention provides a design for the construction of steerable diagnostic catheters. FIGS. 1, 1A and 2 illustrate a bi-directionally steerable catheter with emphasis on the handle portion thereof. The bi-directionally steerable catheter includes a handle 10 formed by a mating first handle half 12 and second handle half 14. The two halfs are joined together using suitable fastening and/or attachment means (not shown). The catheter handle 10 is joined via a cable 16 having an end connector 18 to controlling diagnostic equipment. A cable strain relief means 20 is included at the junction of the cable 16 and the handle 10.

A catheter body 22 is secured in a receiving joint 24 at the front of the handle 10. A catheter strain relief means 26 is included at the receiving joint 24 to reduce the chances of breakage of the catheter body 22. Signal wires 28 (FIG. 2) from ring electrodes (described in more detail following) pass through the interior of the catheter body 22, the handle 10, and the cable 16.

The steering capability of the catheter is provided by a steering lever 30. The steering lever 30 is mounted on a pivot 32 in the handle 10. The ends of the steering lever 30 protrude from the handle 10 through slots 34 (FIG. 1A). In the preferred embodiment, the slots 34 are sealed with rubber 35 having a longitudinally extending slit 33 formed therein through which the handle 30 passes. The rubber seals also serve as a frictional position securing means for the steering lever 30.

As shown in FIG. 2, the steering mechanism of the bi-directionally steerable catheter includes as a key component a continuous length of steering wire 36 extend out of the catheter body 22 and that has its ends 38 secured to the steering lever 30. In the preferred embodiment, the ends 38 of the steering wire 36 pass through holes on opposing sides of the pivot 32 of the steering lever 30. The steering wire ends 38 are affixed to the steering lever 30 by suitable securing means 40 such as set screws or the like. The bi-directionally steerable catheter body 22 may therefore be steered in two directions by rotational manipulation of the steering lever 30 about pivot 32. Full coverage of the vessel or organ being examined is easily obtained by the operator rotating the handle 10 which in turn deflects or steers the distal end portion of the catheter body 22.

Figure 3:
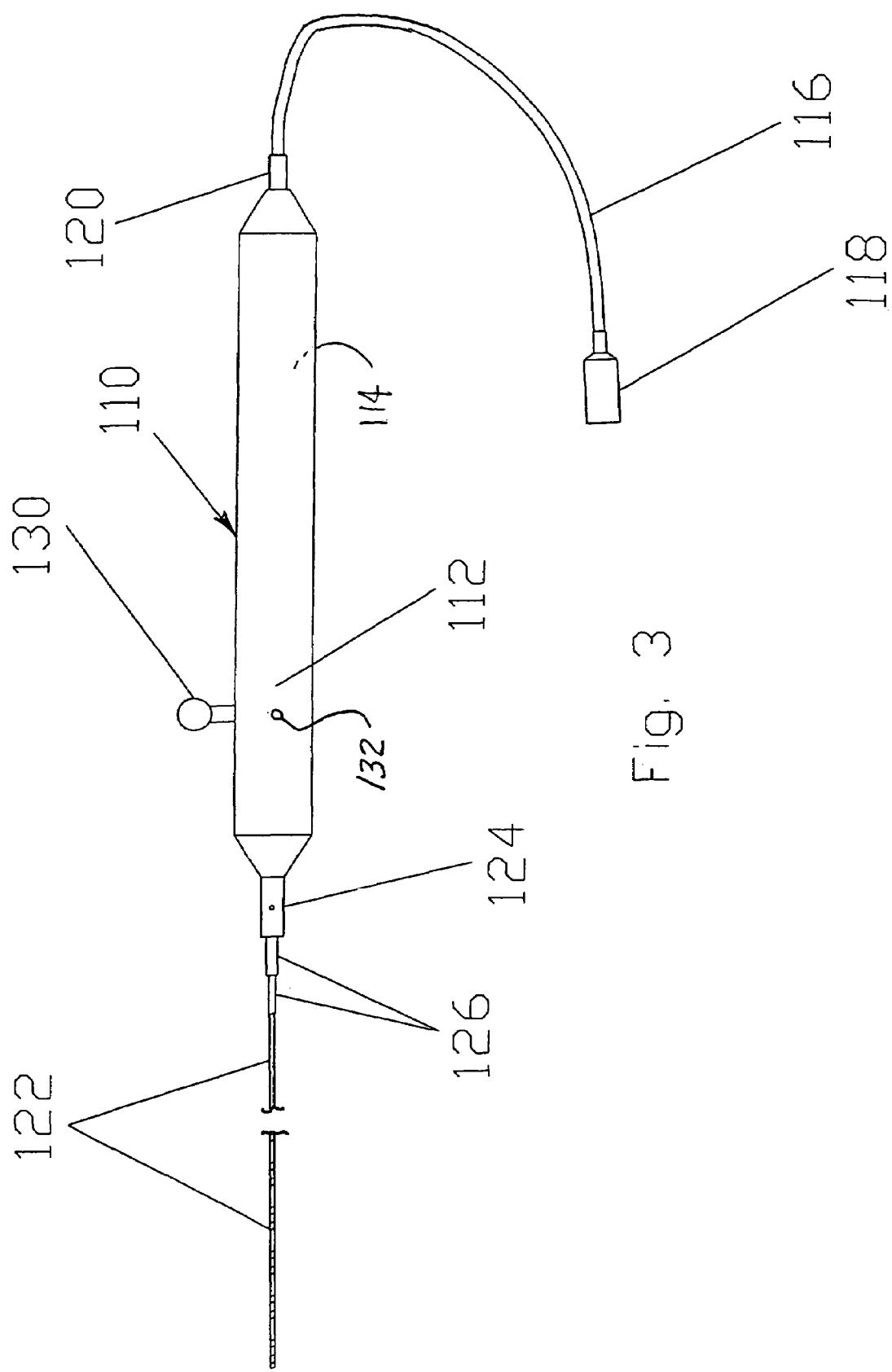
FIG. 3 is a side view of an alternative catheter handle with a unidirectional steering mechanism.
Figure 4:
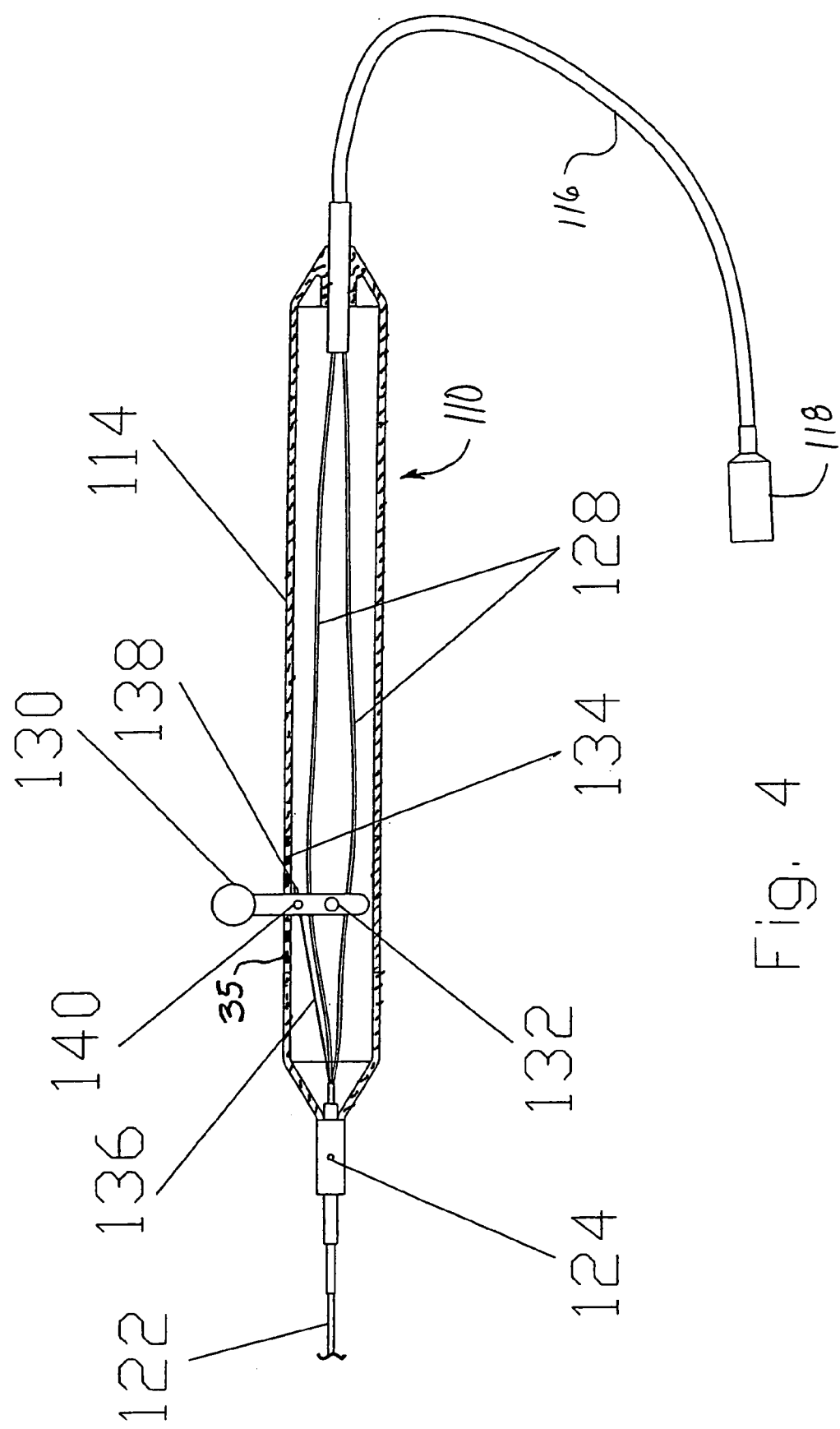
FIG. 4 is a sectional view of the catheter handle of FIG. 3.

FIGS. 3 and 4 illustrate a unidirectionally steerable catheter. As in the previously described embodiment, the unidirectionally steerable catheter includes a handle 110 with a first handle half 112 and a second handle half 114. The unidirectionally steerable catheter handle 110 is coupled via a cable 116 with a connector 118 to the controlling diagnostic equipment. A cable strain relief means 120 is included at the junction of the cable 116 and the handle 110.

A catheter body 122 is secured in a receiving joint 124 at the front of the catheter handle 110. A catheter strain relief means 126 is included at the receiving joint 124 to reduce the chances of breakage of the catheter body 122. Signal wires 128 (FIG. 4) from ring electrodes (again, the ring electrodes and their function will be described in further detail following) pass through the interior of the catheter body 122, the handle 110, and the cable 116.

The steering capability of the unidirectionally steerable catheter is provided by a steering lever 130. The steering lever 130 is rotatably mounted on a pivot 132 in the handle 110. A free end of the steering lever 130 protrudes from the handle 110 through a slot 134. In the preferred embodiment, the slot 134 is sealed with rubber as described above. As with the bi-directionally steerable embodiment, the rubber seal also serves as a frictional position securing means for the steering lever 130.

As with the bi-directional embodiment, the unidirectionally steerable catheter includes as a key component a length of steering wire 136 the proximal end 138 of which is secured to the steering lever 130. In the preferred embodiment, the free end 138 of the steering wire 136 passes through a hole in the steering lever 130. The steering wire 136 is affixed to the steering lever 130 by a steering wire securing means 140. The distal end portion of the catheter body 122 may therefore be steered in one direction by manipulation of the steering lever 130. Steering of the catheter in other directions is easily accomplished by rotation of the handle 110.

Figure 5:
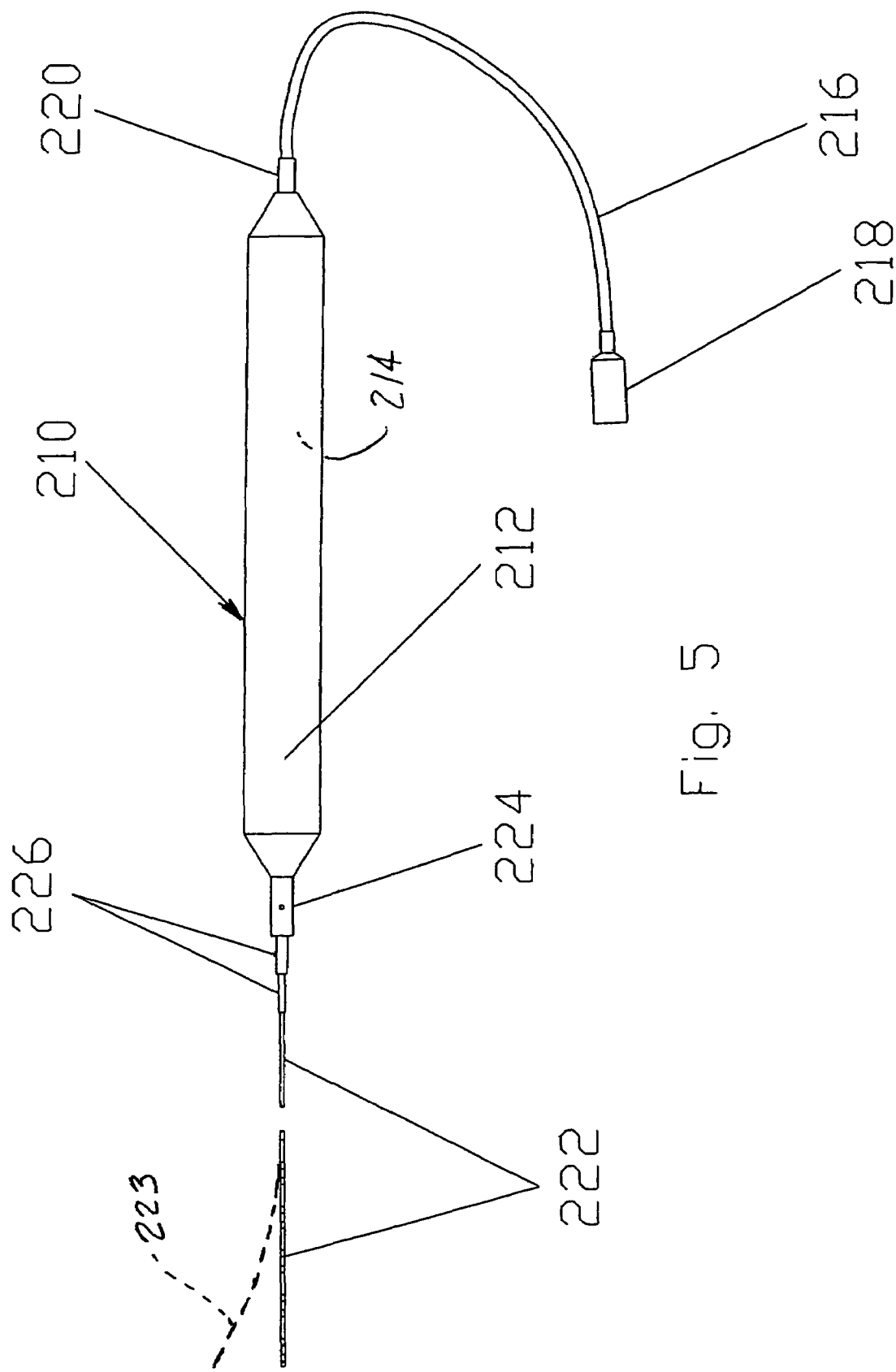
FIG. 5 is a side view of an alternative catheter handle for a fixed-shape distal end catheter.
Figure 6:
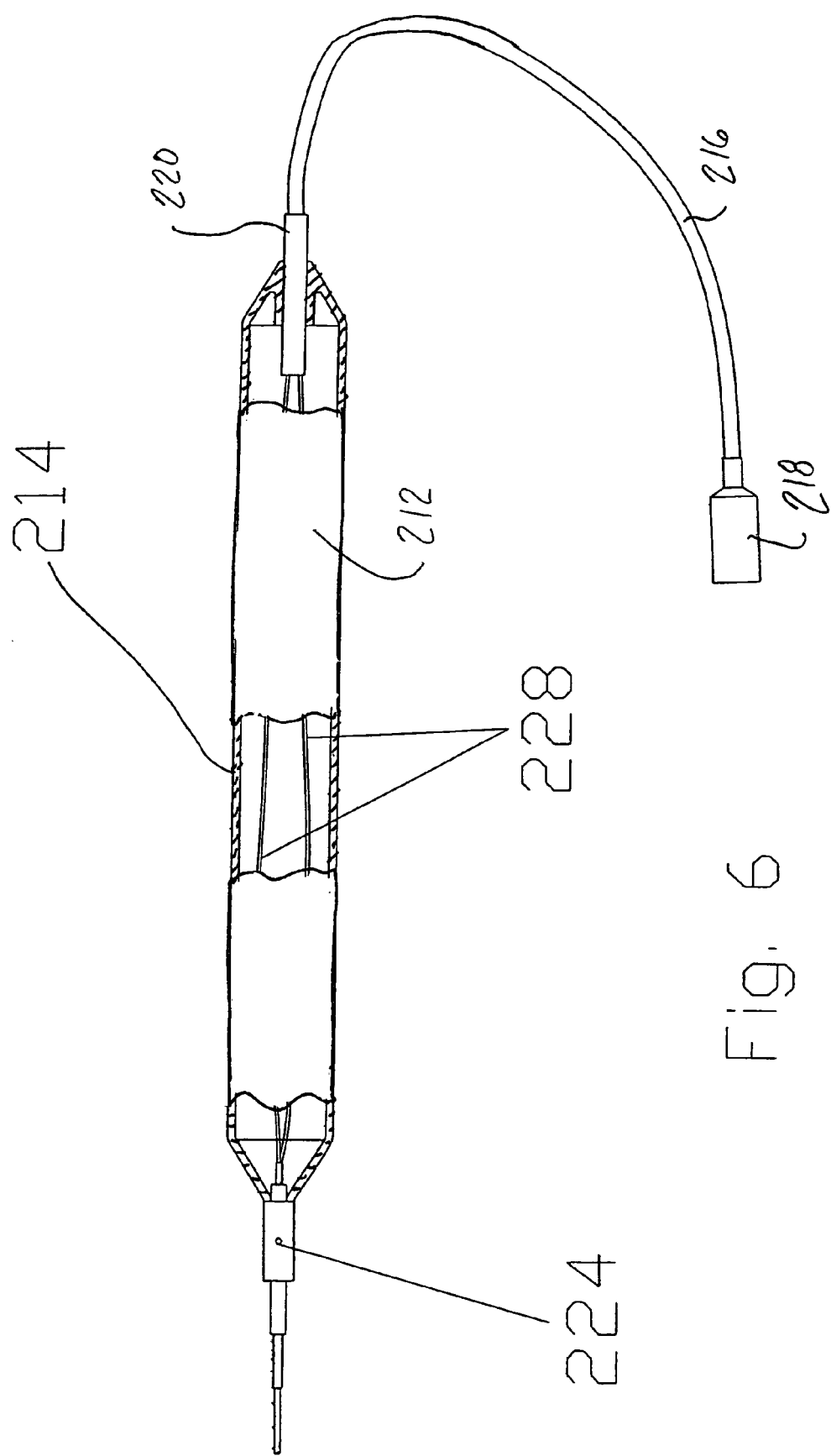
FIG. 6 is a partially broken side view of the catheter handle of FIG. 5.

FIGS. 5 and 6 illustrate a catheter having a distal end of a fixed shape or configuration according to the present invention. This catheter includes a handle 210 having a first handle half 212 and a second handle half 214. The catheter handle 210 is formed similarly to the handles of the bi-directionally and unidirectionally steerable embodiments described above, with a cable 216 and a connector 218 connecting the catheter to the controlling diagnostic equipment. The cable 216 is also provided with a cable strain strain relief means 220 at the junction of the cable 216 and the handle 210.

A catheter body 222 having a fixed distal end configuration (that will be described in detail below) is secured in a receiving joint 224 at the front of the catheter handle 210. A catheter strain relief means 226 is included at the receiving joint 224 to reduce the chances of breakage of the catheter body 222. Signal wires 228 from ring electrodes (described in greater detail following) pass through the interior of the catheter body 222, the handle 210, and the cable 216.

The fixed distal end configured catheter has no steering means, but is formed to the specifications required by the using doctor, e.g. with a specific curvature at the distal end as suggested by the dashed line 223 in FIG. 5. Complete examination of the vessel or organ being examined must be accomplished by the operator's maneuvering of the preformed catheter's handle 210.

FIGS. 7-8B show the detail of the structure of the distal extremity of the catheter body 22 of the bi-directionally steerable catheter of FIGS. 1-2. A proximal portion of the catheter body 22 is covered with a braided tubing 42. The braiding is formed by flat/round wire/thread braided in a suitable pattern that provides high torque transmission and optimal column strength. The distal end or "probe end" of the catheter body 22 is formed by a probe end assembly 45 formed in part by a multi-lumened tubular member 44. A first joint 46 is formed at the point where the proximal portion of the braided tubing 42 meets the probe member 44. A second joint 48 is formed where a distal tip 50 is attached to the distal end of the member 44. The distal tip 50 may be of metal or plastic material and will typically be rounded to ease the insertion of the catheter body 22 into the vessel or organ to be examined. The proximal end portion 49 of tip 50 is generally cylindrical in form and of reduced diameter so that it can be matingly received within the central cavity 54 of probe member 44. End portion 49 has axially extending grooves 51 (see FIGS. 7A and 8A) formed on opposite sides thereof and an opening 53 passing transversely therethrough.

The steering wire 36 and a longitudinally grooved steering wire guide 52 (see FIG. 7A) are contained in the longitudinal central cavity 54 of the probe member 44. Note that steering wire 36 extends along one of the groove 39 of the guide 52, along one of the grooves 51 tip end portion 49, through opening 53 and then back along the other grooves 51 and 39. As tip 50, with steering wire 36 threaded through the opening 53, is inserted into the central cavity 52, interference between the several components in effect fastens the wire 36 to the tip 50. If tip 50 is glued, as with apoxy or the like, to the member 44, additional security of attachment is obtained. The steering wire guide 52 is also generally cylindrical in shape and has a transverse cross section similar to that of the tip end 49 as depicted in FIG. 7A and as indicated above includes two longitudinal grooves as channels 39 to receive and guide the steering wire 36. As tension is applied to the ends of the steering wire 36 by the steering lever 30 of the handle 10 (FIG. 1), the steering wire guide 52 keeps the steering wire 36 separated and properly aligned. The probe member 44 of the catheter body 22 (as shown in FIG. 7C) comprises eleven lumen tubing. The eleven channels form ten passageways 55 for the ten signal wires 28, and the central cavity 54 which contains the steering wire 36 and the steering wire guide 52. The steering wire 36 is anchored to the distal tip 50 as described above.

As is illustrated in FIGS. 7B and 7D, the present invention utilizes a mechanically obtained wire-to-electrode connection method that does not require soldering or welding in order to make and maintain an ohmic electrical contact between each signal wire 28 and a corresponding ring electrode 56. A signal wire support means in the form of a short length of wire 58 is positioned outside the central cavity 54 and dips down into an opening 59 formed in the lumen 55 so as to pass under and force a signal wire 28 through the thin wall 57 outside of lumen 55 into ohmic connection with a ring electrode 56. As the ring is positioned on the resilient member 44, the support wire outside of opening 59 is depressed into mechanical contact with the surface of member 44. A suitable epoxy or glue is applied around the edges of rings 56 to retain the rings in place as well as form seals therebetween. The resiliency of the support wire tends to maintain good ohmic contact between the inner ring surface and the wire 28. In the preferred embodiment, there are ten ring electrodes 56, with a corresponding ten signal wires 28.

FIGS. 8A and 8B show an even simpler method of making an ohmic connection to ring 56 that likewise does not require soldering or welding. To make the connection point illustrated in FIG. 8A, the exposed conductive portion 57 of the signal wire 28 is pulled through opening 59 and folded back onto itself to create an enlarged contact area that forces the signal wire 28 into ohmic contact with the corresponding ring electrode 56 as it is installed on member 44.

Figure 9C:
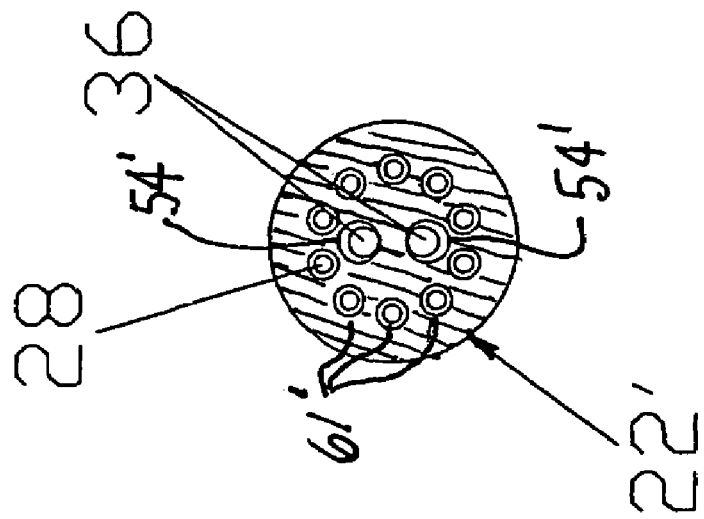
FIG. 9C is a cross section taken along line 9C-9C of FIG. 9B.

FIGS. 9-9C illustrate in some detail the structure of an alternate embodiment of the present invention having a catheter body 22' that likewise forms a bi-directionally steerable catheter means. As with the first embodiment, a proximal portion of the catheter body 22' is formed by a braided tubing 42'. A distal or probe end assembly 45' of the catheter body 22' is formed by a tubular member 44' having a pair of longitudinally extending lumens 54' formed therein through which the steering wire 36 is passed. A first joint 46' is formed at the point where the braided proximal portion 42' meets the probe end member 44'. A second joint 48' is formed where a distal tip 50' is attached to the member 44'.

As opposed to the first embodiment of the bi-directionally steerable unit, in this embodiment, a separate steering wire guide (52 in FIGS. 7 and 7A) is not utilized. As is perhaps best illustrated in FIGS. 9 and 9A, the distal tip 50' contains no anchoring means for the steering wire 36. In this embodiment, the steering wire 36 is passed through two separate longitudinal passageways 54' formed in the central portion of the member 44'. The steering wire guide is completely eliminated so as to simplify the manufacturing process. In this embodiment, the steering wire 36 is simply threaded through one lumen 54' out of the distal end 48' of the member 44' and then looped back through the other lumen 54', where it pulls against and deforms the material 60' in the central area of the probe member 44'. A flat or rounded ended end cap 50' is then installed over the end of member 44' and fixed in place by epoxy or the like. The end cap 50' may be a soft tip, or a metal tip to form an additional electrode. The probe member 44' of the catheter body 22' as shown in FIG. 9C is comprised of a twelve lumen tubing, the twelve channels thereof including the ten lumens 61' containing the ten signal wires 28, and the two lumens 54' containing the two portions of the steering wire 36.

Figure 9B:
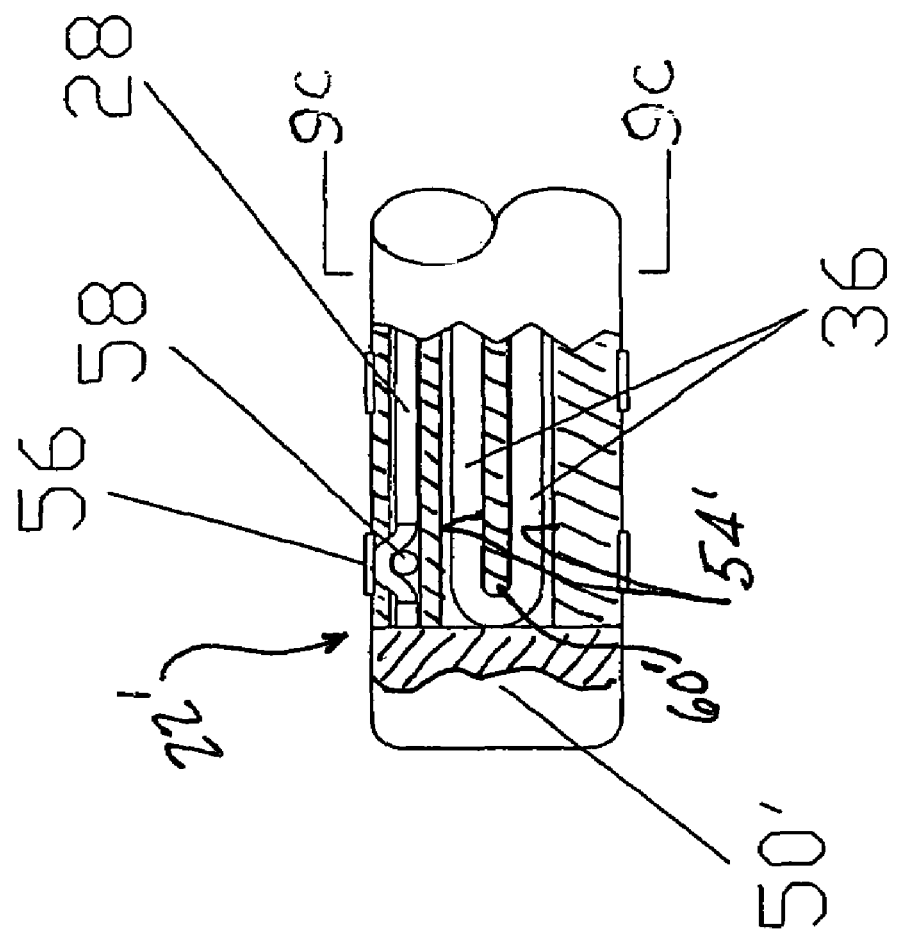
FIG. 9B is a broken sectional showing interior details of FIG. 9.

As illustrated in FIG. 9B, the probe end assembly 45' of this embodiment also utilizes the solderless (weldless) connection method to make a contact point between each signal wire 28 and a corresponding ring electrode 56 as in the first bi-directionally steerable embodiment described above.

Figure 10D:
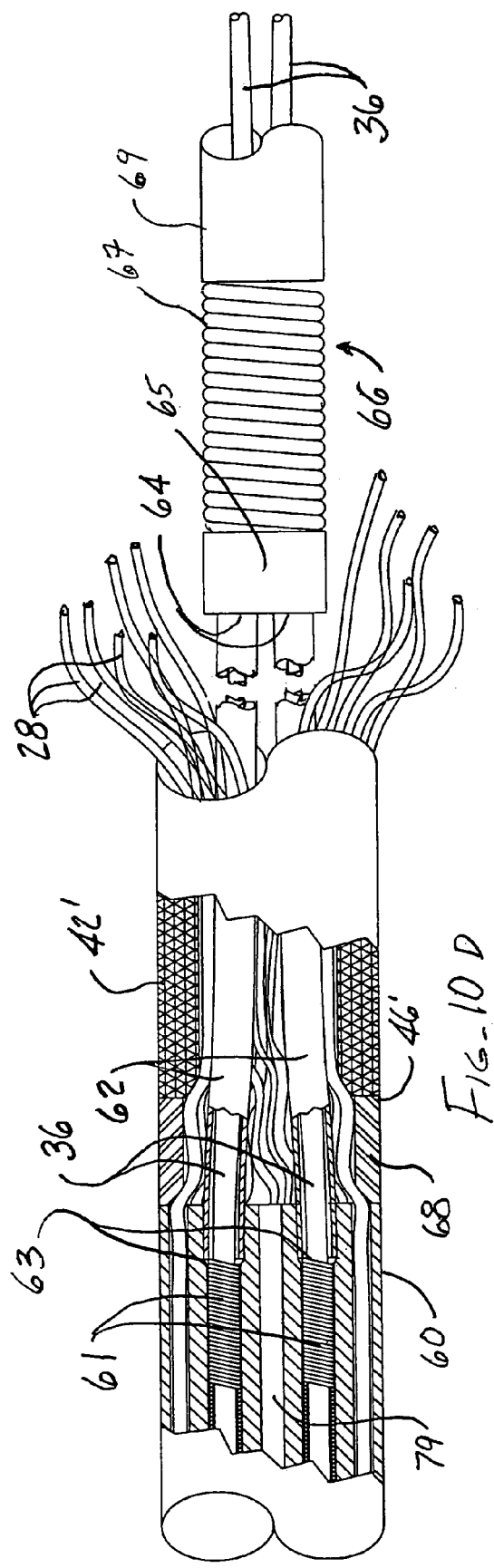

FIGS. 10A-10D illustrate a 20 wire (electrode) alternative embodiment of the invention similar to that of FIGS. 9-9C except that in this embodiment a pair of tempered coil springs 61 are disposed within the control wire lumens 54' of member 60 to provide compression control of the steerable probe member. The distal ends of the springs are engaged by the ends of a C-shaped tube 37 (FIG. 10B) through which the wire 36 also extends as it passes from one spring 61 to the other. However, frictional engagement of the wire 36 with the tube 37, and the engagement of the tube 37 to the end of member 60 in effect form an attachment of the steering wire to the distal end of the member 60 and tend to avoid slippage of the steering wire at the probe tip during steering. The proximal ends of the springs 61 bear against steel tubes 62 at 63 as shown in FIG. 10D, the proximal ends of which are welded at 64 to a fitting 65 that is attached to the distal end of a coil spring 67 forming of a strain relief device 66 attached to the distal end of a long tube 69. The tube 69 leads back to and is attached to the handle 10 (FIGS. 1-4). The helical spring 67 provides for articulation of the proximal shaft enabling it to access certain hard to reach intracardial substrates. The relief device and the tubing 69 are contained within the proximal tubing attached to the handle 10. The tubing 69 and device 66 together with tubes 62 provide compression control of the catheter shaft during steering of the steerable distal probe member 60 (FIG. 10A).

In order to provide the improved deflection control a longitudinally extending lumen 79 is formed in member 60 and is generally rectangular transverse cross-section concentric with the axial center lumen 79 extends from one end of the flexible member 60 to the other. The long dimension of the rectangular cross-section is directed orthogonal to the longitudinal plane including the control wire lumens 54'. Consequently, flexibility of the member 60 in the directions of the control wires in enhanced relative to any tendency to deflect "out of plane" during steering. In other words, the rectangular lumen 79 in uniplaner deflection (steering) of the member 60.

FIGS. 11A-11D illustrate still another alternative embodiment of the invention having enhanced compression control and deflection direction control. In this case improved compression control is achieved by using a single coaxial disposed and longitudinally extending coil spring 70 along the longitudinal axis of probe member 72. The spring 70 is constrained by distally mating it at 71 to the steering wire's looped distal end and proximally fixing the opposite end to the proximal end of the probe member 72. To improve deflection direction control, a continuous length of control wire 74 having a semi-circular or D-shaped transverse cross-section is utilized and extended through conforming lumens 78 likewise having D-shaped transverse cross-section. The flat surfaces 76 of the left and right (FIG. 11B) or upper and lower (FIG. 11D) portions of the control wire face the neutral plane 75 about which the catheter may be deflected.

Note also that flexibility of the deflectable probe member 72 is also enhanced by positioning the electrode wires 28 and their associated lumens as close to the neutral plane as is possible so that minimal longitudinal stress is applied thereto as the probe member 72 is steered.

FIGS. 12-15 illustrate an embodiment of a unidirectionally steerable catheter in accordance with the present invention. As with the above described bi-directionally steerable versions, a proximal portion 142 (FIG. 12) of the catheter body 122 is covered with a braided tubing 142. A distal or probe end assembly 145 of the catheter body 122 is formed in part by a multi-lumened tubular member 144. A first joint 146 is formed at the point where the distal end of tubing 142 meets the proximal end of probe end of member 144. A second joint 148 is formed where a distal tip 150 is attached to the probe member 144.

As is additionally shown in FIGS. 13-15, the single steering wire 136 and a tempered straight spring wire or coil shown schematically at 160 are respectively contained in two separate longitudinal passageways 153 and 154 of the probe end member 144. The distal end of the steering wire 136 is affixed to the distal end of the spring wire or coil 160 at 161 (FIGS. 12-14). A user steers the unidirectional catheter body 122 by operating the steering lever 130 (FIG. 4) so as to apply tension to the steering wire 136, which causes the probe end member 144 to be deflected. When the user releases the tension, the spring wire or coil 160 returns the catheter body 122 to its at-rest position. The probe end member 144 shown in FIG. 15 is comprised of a twelve lumen tubing, the twelve channels forming ten lumens utilized to contain ten signal wires 28, and two passageways 153 and 154 respectively containing the steering wire 136 and the spring wire or coil 160.

FIGS. 14 and 15 confirms that the unidirectional embodiment also utilizes a solderless (welderless) connection method to make ohmic contact between each signal wire 28 and a corresponding ring electrode 56. As in the bi-directional embodiment, a signal wire support means 58 extends into a hole in the wall of member 144 outside the central passageways 153 and 154 so as to force a signal wire 28 into ohmic connection with a ring electrode 56. In the illustrated embodiment, there are ten ring electrodes 56, with a corresponding ten signal wires 28.

Figure 16:
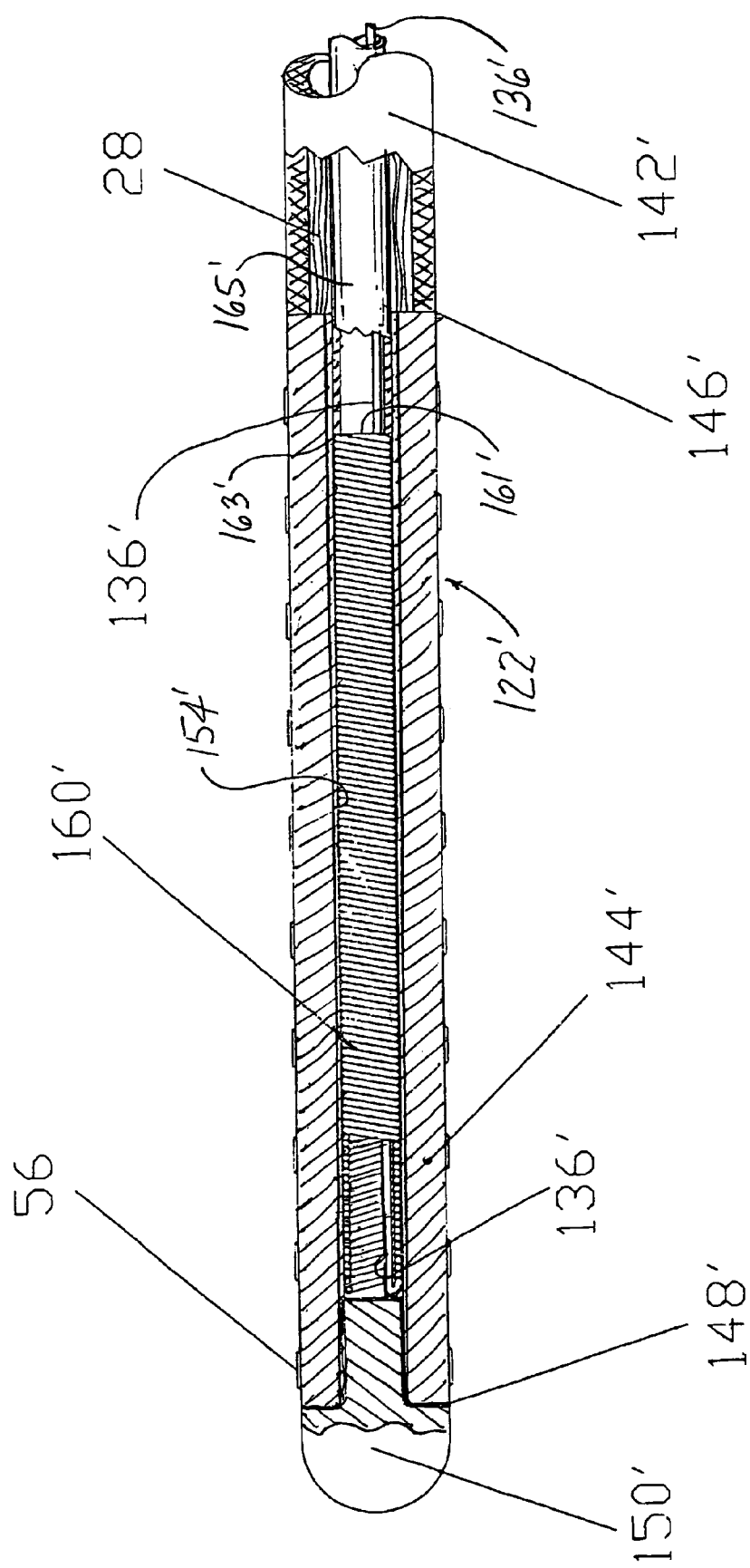
FIG. 16 is a sectional view of a second embodiment of a unidirectional steerable catheter.

FIGS. 16-18 illustrate the catheter body 122' of an alternate embodiment of the unidirectionally steerable catheter. As with the first embodiment of a unidirectionally steerable version, a proximal portion 142' of the catheter body 122' is covered with a braided tubing, and a distal probe end assembly 145' is formed by a multi-lumened tubular member 144'. A first joint 146' is formed at the point where the proximal portion 142' meets the probe member 144'. A second joint is formed at 148' where an end cap 150 is affixed to the distal end of member 144'.

The single steering wire 136' is comprised of a linear segment of the spring wire used to form an open or loosely pitched helical coil spring 160' and is folded back to extend through the spring to the handle (not shown). Both the steering wire 136' and the spring 160' are also loosely contained in a longitudinally extending central cavity 154' of the member 144', as is additionally shown in FIGS. 17 and 18. The proximal end 161' of spring 160' butts against the distal end 163' of a tube 165' so as to control compression. Because of the loose containment, loose or open pitch of the spring 160' and the off center "attachment" of the wire portion 136' to spring 160', pulling on the wire 136' causes the spring 160' and thus the member 144' to deflect. Due to its resiliency the helical coil spring 160' also serves to return the catheter body 122' to its at-rest position after the user releases the steering tension. The catheter body 122' shown in FIGS. 16-18 is comprised of eleven lumen tube.

As shown in FIG. 17, the second embodiment of the unidirectionally steerable catheter probe end assembly 145' also utilizes a solderless (weldless) connection method to make ohmic contact between each signal wire 28 and a corresponding ring electrode 56.

Figure 19:
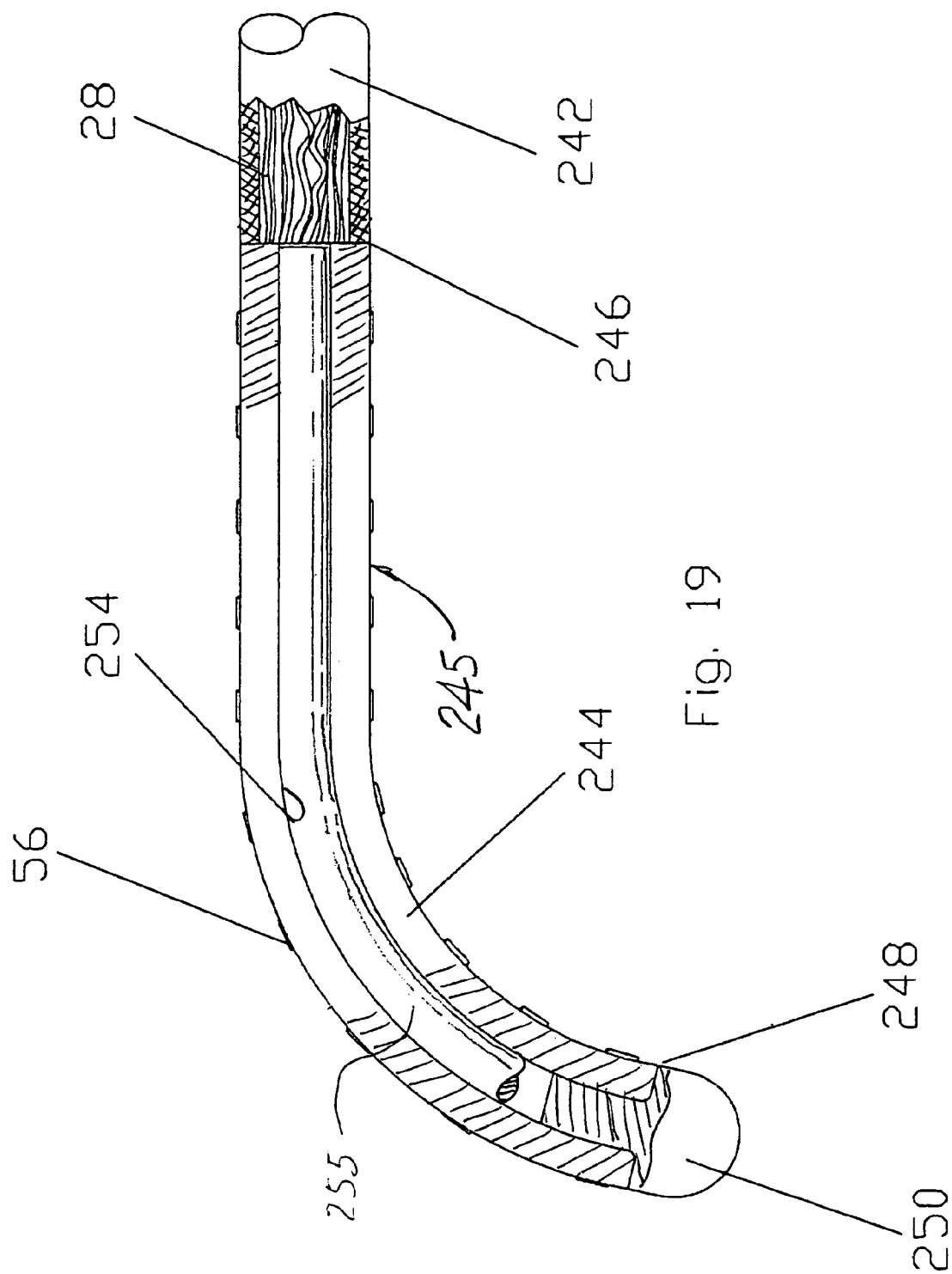
FIG. 19 is a sectional view of a fixed-shape distal end catheter.
Figure 24:
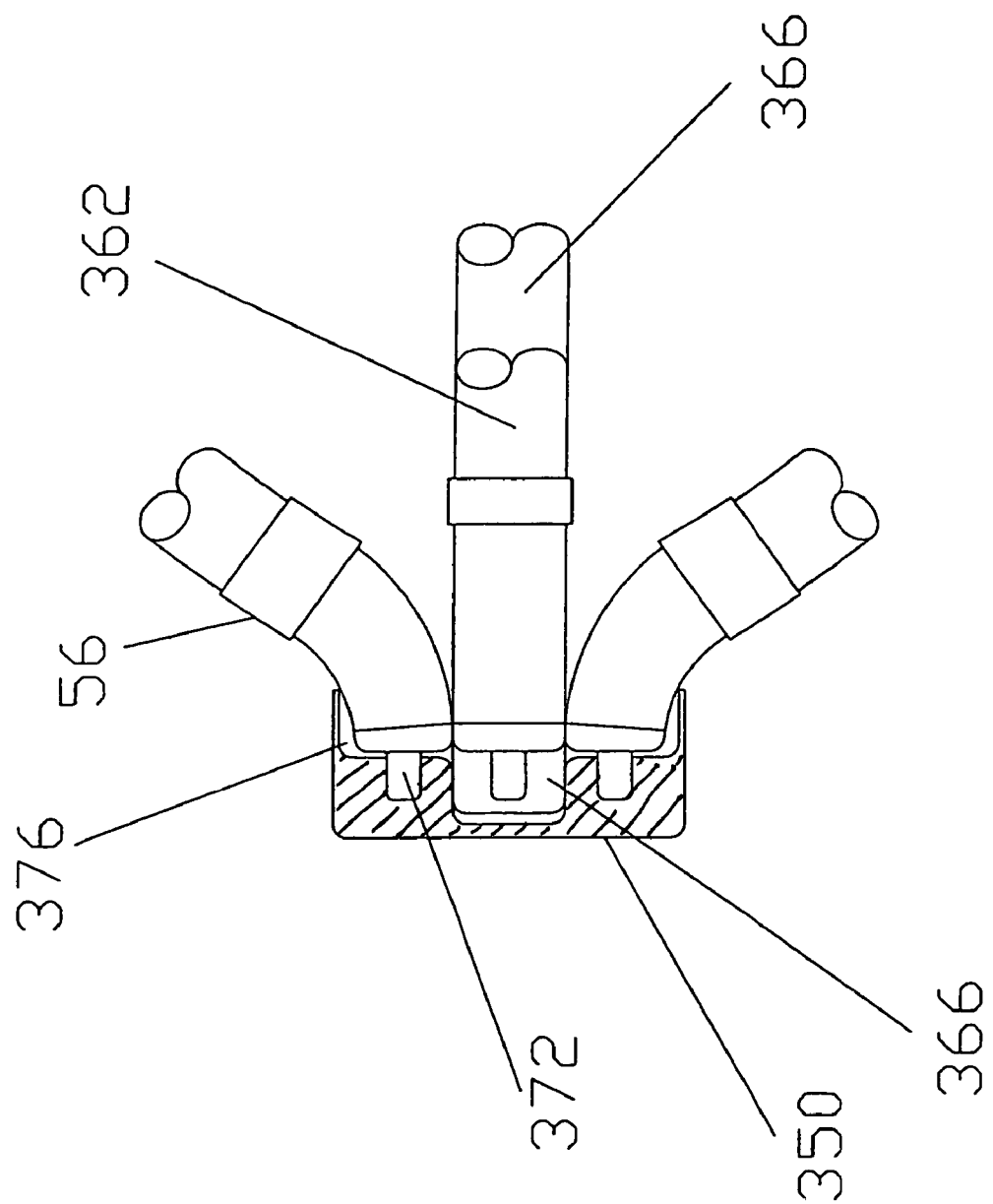
FIG. 24 is a sectional view of the distal tip of the basket catheter of FIG. 22 with splines inserted.

FIGS. 19-21 illustrate the structure of a fixed curve shaped catheter probe end assembly 245. The structure of the catheter body is equivalent to that of the steerable embodiments, with a proximal portion of the catheter body covered with a braided tubing 242, and a distal or probe end member 244 of the catheter body formed by an eleven lumen tube. A first joint 246 is formed at the point where the distal end of tubing 242 meets the proximal end of the probe member 244. The fixed curve shaping of the probe member portion of the catheter body is accomplished by forming a deformable member 255, such as a spring or flexible rod, or even a rubber or plastic material in a state or condition such that when cooled or cured it will form a curved member that is flexible but has memory and returns to its curved configuration when at rest. In practice, a straightening sheath (not shown) is typically used to aid in the insertion of the shaped probe member into the vessel or organ under examination. After the catheter probe member is properly positioned the sheath is pulled back along the catheter body to expose the member 244 and allow it to return to its curved configuration.

As shown in FIG. 20, the curved probe member also uses the unique solderless (weldless) connection method to create a mechanically obtained ohmic contact between each signal wire 28 and a corresponding ring electrode 56.

In order to reduce the number of types of tubing required to be stocked for manufacture of the catheter bodies, the curved probe members are also constructed using eleven lumen tubing. As indicated above, the central longitudinal opening 254 is filled with a deformed or deformable object or filler material. As indicated above, the filler material can be a wire or other material that is pre-formed, or that is formed to a desired shape after it is inserted into the tubing.

FIGS. 22-33 depict a basket catheter embodiment including features assembled in accordance with the present invention. The distal or probe end assembly 345 comprises a plurality of splines 362 (in this case 4) that expand to form the basket of the catheter. Each of the splines 362 includes a plurality of ring electrodes 56 to transmit scanned data. A proximal end of each of the splines 362 is received in a coupling ferrule 364, and a distal end of each of the splines 362 is received in a distal tip 350. At least one retractable and steerable central member 366 extends through a central opening in the coupling ferrule 364.

Figure 26:
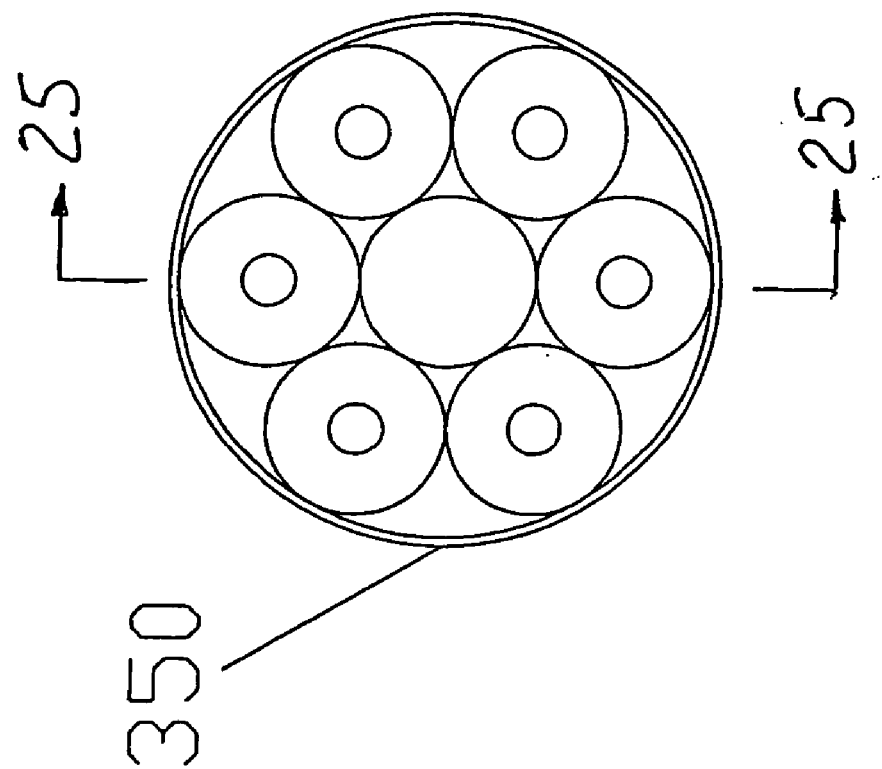
FIG. 26 shows an inside end view of the distal tip shown in FIG. 25.
Figure 25:
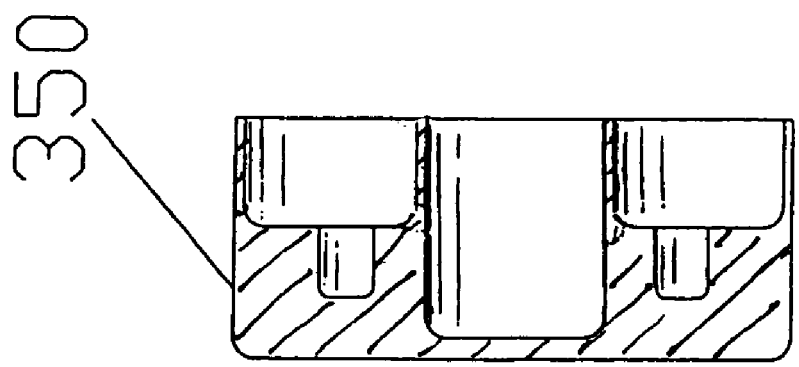
FIG. 25 is a sectional view of the distal tip of the basket catheter of FIG. 22.
Figure 29:
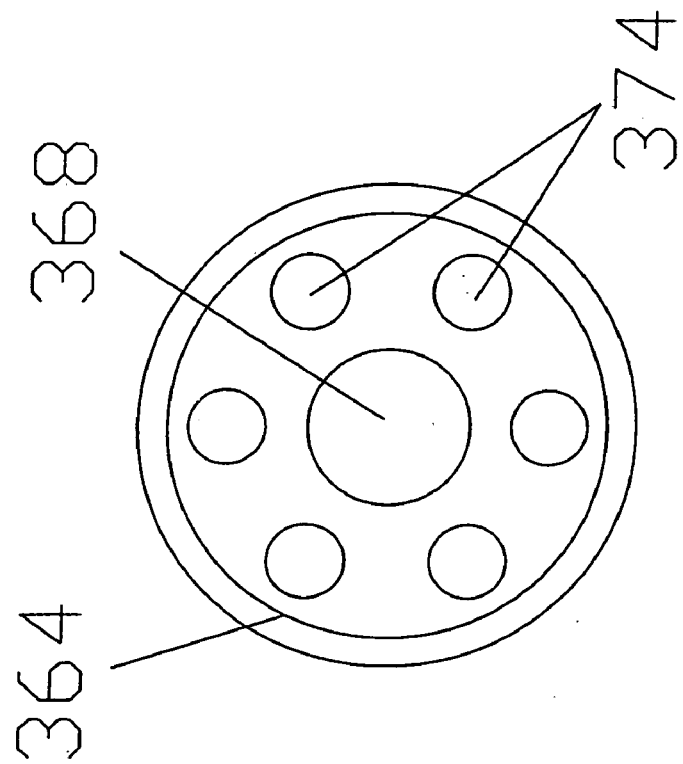
FIG. 29 is a proximal end view of the coupling ferrule looking in the direction of arrows 29-29 of FIG. 28.
Figure 28:
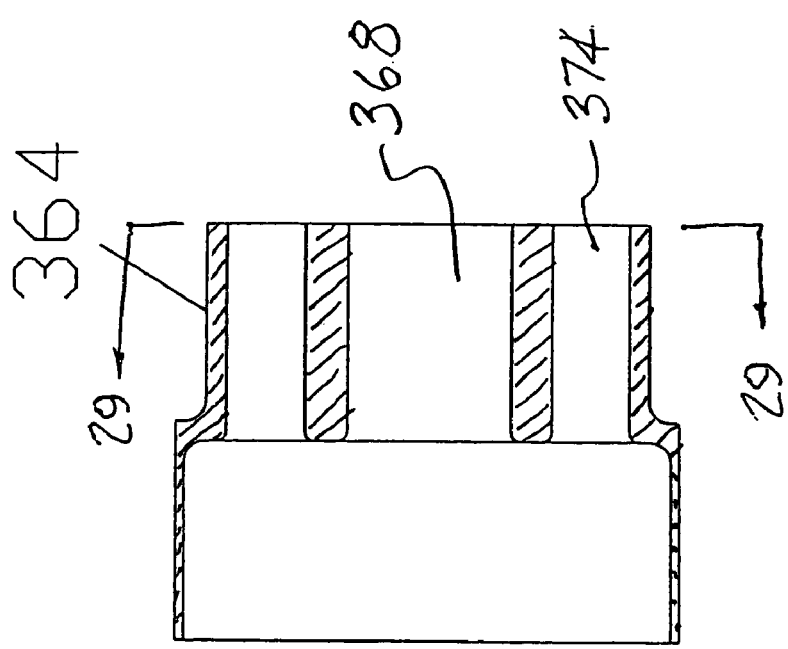
FIG. 28 is a sectional view of the coupling ferrule shown in FIG. 27.

The distal ends of the splines 362 and the central member 366 are secured to the distal tip 350 by means of thermal bonding or the use of a sealant/adhesive 370. The distal tip 350 with the distal ends of the splines 362 and the central member 366 therein is shown in detail in FIG. 24 wherein the basket forming splines 362 are shown in the expanded position. Each of the splines 362 includes a spring wire 372 that extends along the length thereof. The spring wires 372 will typically be soldered to secure them in the distal tip 350. The spring wires 372 provide a conformal force so that the basket splines conform to the surfaces being inspected. Longitudinal and axial cross section views of the distal tip 350 are shown in FIGS. 25 and 26.

The proximal ends of the splines 362 are secured in the coupling ferrule 364 at a transition region in the ferrule by sealant/adhesive 370 or thermal bonding. The signal wires 28 extend out of the splines 362 through holes 374 (FIGS. 28, 29) in the ferrule 364 and into the lumens in the proximal portion 342. As illustrated in FIG. 27, the signal wires 28 are protected in tubing 29 before entering the proximal portion of the basket catheter. In order to provide a seal between the ferrule 364 and the retracting central member 366, an appropriate sealing compound 390 is applied to the central hole 365 of the ferrule 364.

The central member 366 is essentially a bi-directionally steerable catheter configured as illustrated in FIGS. 7-11 and whose distal end 381 (FIG. 30A) is contained in the tip 350 forming the probe end. In order to provide steering capability to the basket catheter, a continuous length of steering wire 336 is provided in passageways 354 of the central member 366 (see also FIG. 31).

Figure 30:
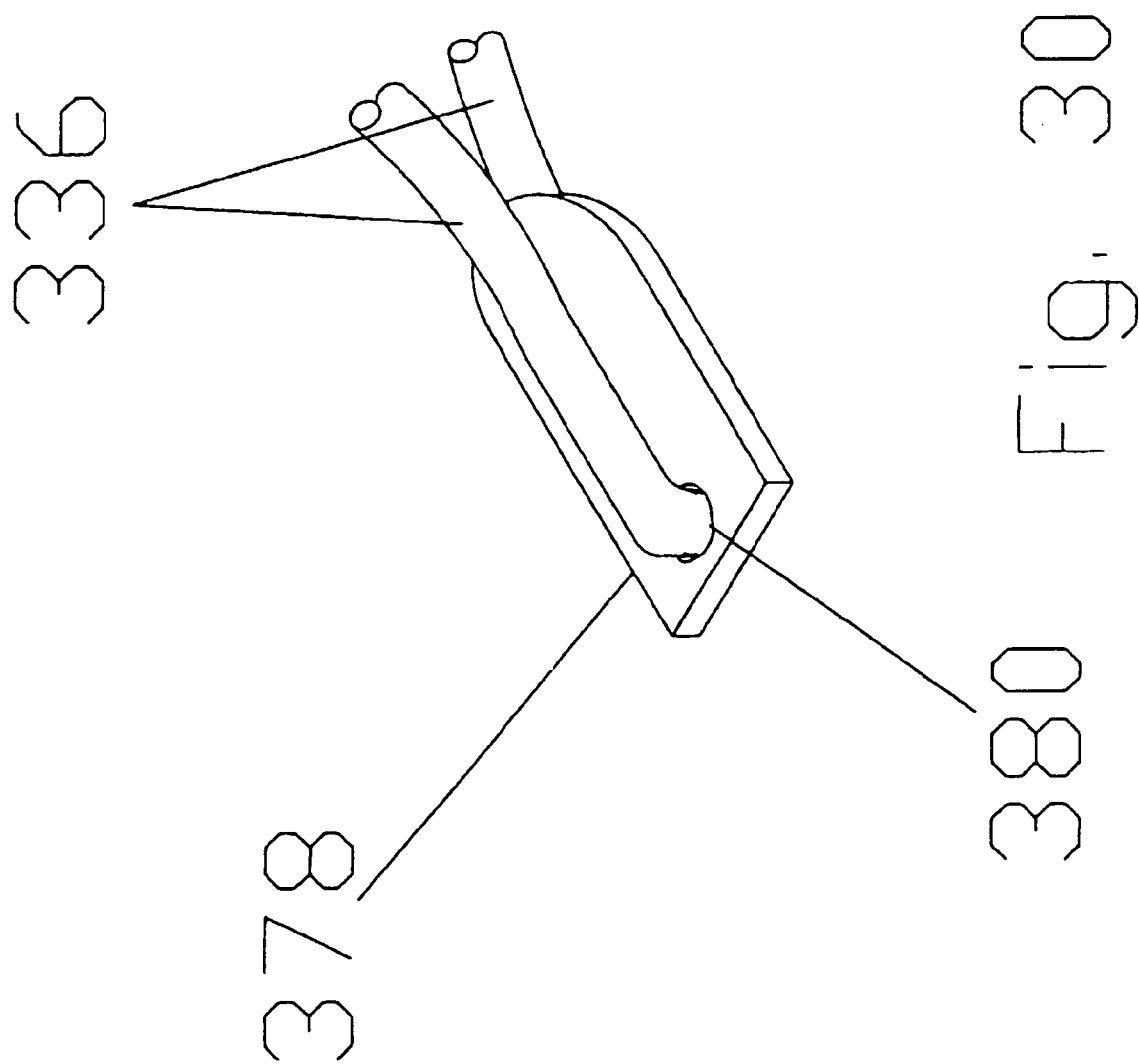
FIG. 30 is a perspective view of a steering wire anchor means.

As is shown in FIGS. 30 and 30A, the steering wire 336 is passed through a hole 380 in and is secured to a steering wire anchor 378 that is embedded in the end of a rectangular lumen 379 at the end of the retractable central member 366 that is affixed to the distal tip cap 350. As in the embodiment illustrated in FIGS. 10A-10D described above, the rectangular lumen 379 also aids in uni-planer deflection of the steerable basket.

Figure 33:
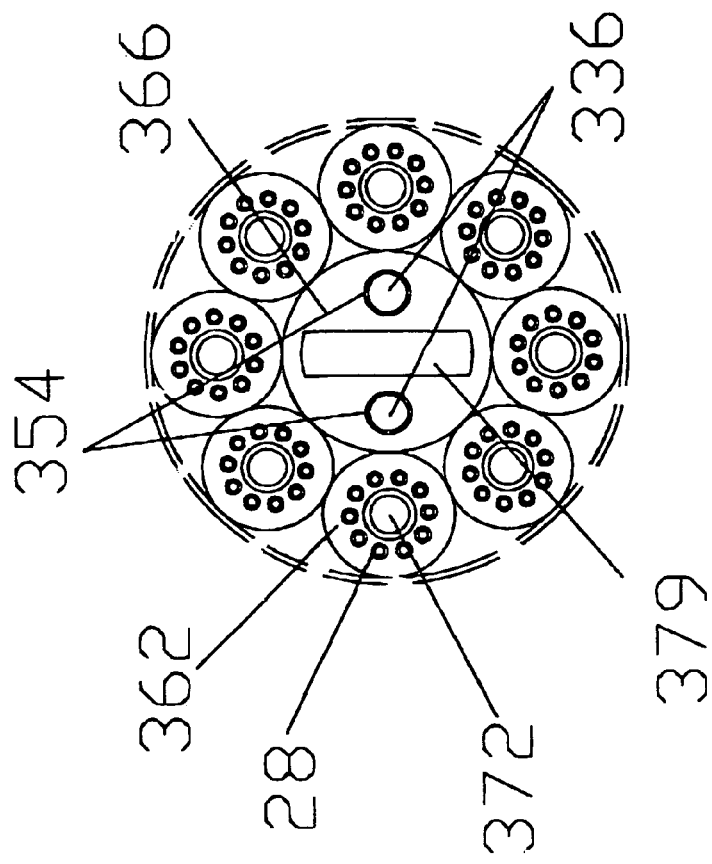
FIG. 33 is a cross sectional view of a basket catheter with eight splines.
Figure 32:
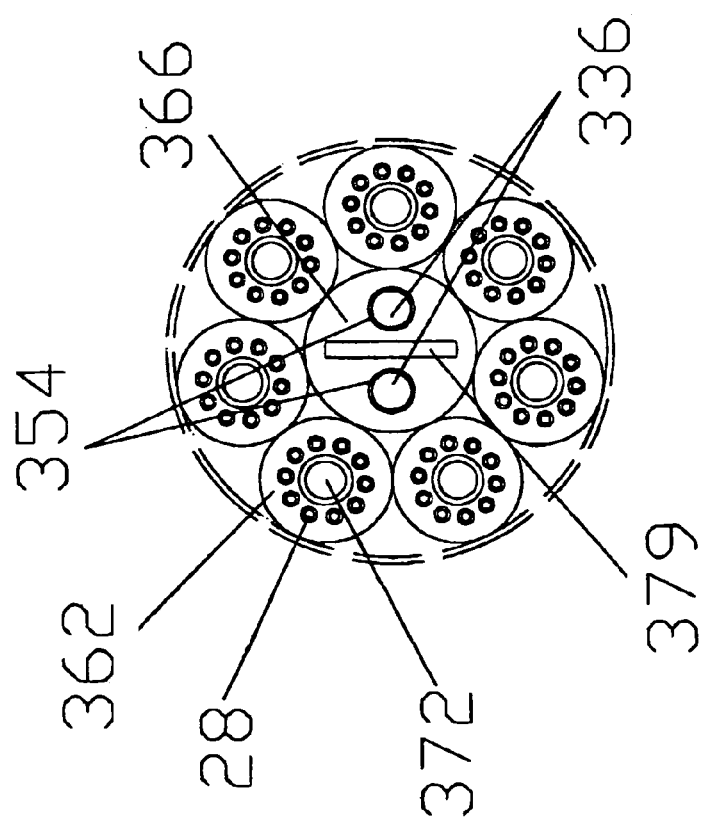
FIG. 32 is a cross sectional view of a basket catheter with seven splines.

The number of splines utilized in the basket of the catheter can of course vary according to the needs of the user. FIG. 31 shows a cross section of the basket catheter with a six spline embodiment. FIG. 32 illustrates a seven spline embodiment, and FIG. 33 depicts an eight spline embodiment.

To expand the basket catheter from the at rest position shown in FIG. 22, the user applies an expanding force to the basket by movement of the central member 366 relative to the proximal portion 342 as suggested by the arrow A1 in FIG. 23. This causes the outer splines 362 of the catheter to expand to the position shown by the solid lines in FIG. 23. Note that the basket can also be deflected downwardly (in the direction of arrow A2), as shown by the dashed lines, by use of the control wires 336. Similarly, the basket can be deflected upwardly in the direction of arrow A3.

Figure 35:
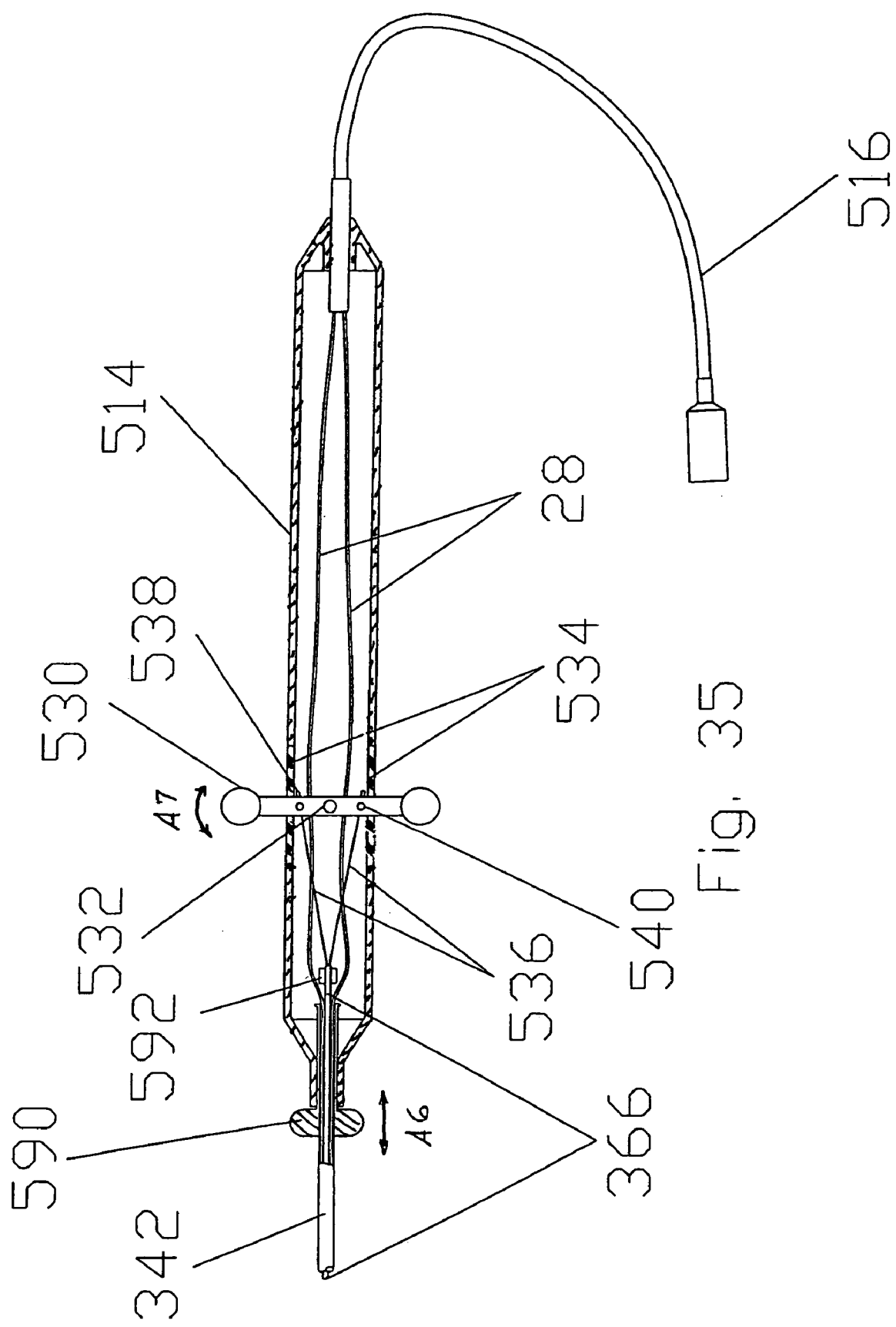
FIG. 35 is a cross sectional view of another handle for a retractable and steerable basket catheter.

Control mechanisms used to accomplish the expansion and deflection of the basket are shown in FIGS. 34 and 35. FIG. 34 illustrates a handle 414 that includes a pair of elongated slots 434 through which a steering lever 430 extends. A slider 490 to which the handle 414 is pivotally affixed is movably disposed within the handle 414. An attachment fixture 492 receives the proximal end of the central member 366 and secures it to the slider 490. The ends 438 of the steering wire 436 pass through channels 437 in the slider 490 and are secured to the steering lever 430 on opposite sides of a pivot 432 by suitable securing means 440.

The signal wires 28 pass from the proximal portion 342 of the catheter openings (not shown) in through the handle 414 and into a cable 416. The signal wires 28 are not secured to the slider 490. The user applies expanding tension to the basket by sliding the steering lever 430 and block 490 back in the handle 414. Steering the catheter is accomplished by rotating the steering lever 430 about the pivot 432 as suggested by the arrow A5.

FIG. 35 illustrates an alternative embodiment of the control handle in which a slider 590 is affixed to the proximal end of the catheter body 342 and is telecopically slideable relative to handle 514. The central member 366 is secured to the handle 514 at 592. The ends of control wire 536 are secured to a steering lever 530 pivotally affixed to handle 514 by a pivot 532. Inasmuch as the device shown in FIG. 35 is also a bi-directionally steerable unit, the handle 514 includes a pair of slots 534 through which the steering lever 530 extends. Expansion and contraction of the basket catheter (as in FIG. 23) is accomplished by moving the slider 590 away from and back to the handle 514 as suggested by the arrow A6. Steering of the catheter is accomplished by rotating steering lever 530 about the pivot 532 and within the slots 534 as indicated by arrow A7.

The signal wires 28 are loosely contained in the handle and pass from the proximal portion 342 of the catheter through the handle 514 and into a cable 516.

Although the present invention has been particularly shown and described above with reference to specific embodiments, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A steerable diagnostic catheter comprising:
   an elongated, tubular central member having a distal end and a proximal end, said central member having a deformable end portion proximate said distal end;
   a catheter body having a proximal portion and a distal portion enveloping said central member, said distal portion including a probe assembly formed by
      a plurality of deformable lengths of multi-lumened tubing forming splines disposed in parallel and surrounding relationship to the deformable end portion of said central member, each said length of multi-lumened tubing having a first end affixed to the distal end of said central member by an end cap, and a second end affixed to the distal end of said proximal portion of said catheter body, and
      a plurality of electrodes distributed along the length of each spline, said electrodes being formed by circumscribing metal rings;
   a handle affixed to the proximal end of said catheter body, and including a steering actuator and a slider means for enabling relative axial movement between said proximal portion and said central member;
   a plurality of signal wires extending through said handle, said proximal portion and the lumens of said splines, a distal end portion of each said signal wire being deformed and extending through an opening in the outer wall of its corresponding tubing, said deformed portion being ohmically connected to one of said rings by mechanical engagement thereto, wherein said mechanical engagement of each said ring to a corresponding signal wire is achieved by folding said deformed portion back upon itself such that interference of the folded portion with the deformed portion maintains mechanical engagement of the folded portion to the ring;
   at least one steering wire having a first end affixed to said steering actuator and extending therefrom through said central member, a second end of said at least one steering wire being affixed to the distal end of said central member;
   whereby movement of said slider means in a first direction causes contraction of said distal portion of said catheter body resulting in deployment of said lengths of multi-lumened tubing away from central member, and whereby manipulation of said steering actuator causes retraction or extension of said at least one steering wire resulting in deformation of said deformable end portion and said probe assembly thereby enabling said catheter to be steered.

2. A steerable diagnostic catheter as recited in claim 1 wherein said each of the spline forming tubes includes a central lumen having a length of spring wire disposed therein to provide conformal forces causing the splines to conform to the surfaces being inspected.

3. A steerable diagnostic catheter as recited in claim 1 wherein said steering actuator is pivotably mounted to said handle.

4. A steerable diagnostic catheter as recited in claim 1 wherein said steering actuator is pivotably mounted to said slider means.

5. A steerable diagnostic catheter as recited in claim 1 wherein said steering actuator is pivotably mounted to rotate about a pivot pin disposed within said handle and extends through a slot formed therein.

6. A steerable diagnostic catheter as recited in claim 5 wherein said first end of said steering wire is connected to said steering actuator on one side of said pivot pin, extends through said central member to the distal end thereof where it engages said central member, and then back through said central member to said handle where a second end thereof is connected to said steering actuator on an opposite side of said pivot pin, whereby movement of said steering actuator in one direction causes deflection of said probe assembly in one direction and movement of said steering actuator in an opposite direction causes deflection of said probe assembly in another direction.

7. A steerable diagnostic catheter comprising:
   an elongated, tubular central member having a distal end and a proximal end, said central member having a deformable end portion proximate said distal end;
   a catheter body having a proximal portion and a distal portion enveloping said central member, said distal portion including a probe assembly formed by
      a plurality of deformable lengths of multi-lumened tubing forming splines disposed in parallel and surrounding relationship to the deformable end portion of said central member, each said length of multi-lumened tubing having a first end affixed to the distal end of said central member by an end cap, and a second end affixed to the distal end of said proximal portion of said catheter body, and a plurality of electrodes distributed alone the length of each spline, said electrodes being formed by circumscribing metal rings;

a handle affixed to the proximal end of said catheter body, and including a steering actuator and a slider means for enabling relative axial movement between said proximal portion and said central member;

a plurality of signal wires extending through said handle, said proximal portion and the lumens of said splines, a distal end portion of each said signal wire being deformed and extending throuah an opening in the outer wall of its corresponding tubing, said deformed portion being ohmically connected to one of said rings by mechanical engagement thereto, wherein said mechanical engagement of [said] each said ring to a corresponding signal wire is facilitated by a short length of wire partially wrapped about the corresponding tubing, passing beneath said deformed portion and lying between the ring and the tubing;

at least one steering wire having a first end affixed to said steering actuator and extending therefrom through said central member, a second end of said at least one steering wire being affixed to the distal end of said central member;

whereby movement of said slider means in a first direction causes contraction of said distal portion of said catheter body resulting in deployment of said lengths of multi-lumened tubing away from central member, and whereby manipulation of said steering actuator causes retraction or extension of said at least one steering wire resulting in deformation of said deformable end portion and said probe assembly thereby enabling said catheter to be steered.

8. A steerable diagnostic catheter comprising:

an elongated, tubular central member having a distal end and a proximal end, said central member having a deformable end portion proximate said distal end;

a catheter body having a proximal portion and a distal portion enveloping said central member, said distal portion including a probe assembly formed by a plurality of deformable lengths of multi-lumened tubing forming splines disposed in parallel and surrounding relationship to the deformable end portion of said central member, each said length of multi-lumened tubing having a first end affixed to the distal end of said central member by an end cap, and a second end affixed to the distal end of said proximal portion of said catheter body, and a plurality of electrodes distributed along the length of each spline, said electrodes being formed by circumscribing metal rings;

a handle affixed to the proximal end of said catheter body, and including a steering actuator and a slider means for enabling relative axial movement between said proximal portion and said central member;

a plurality of signal wires extending through said handle, said proximal portion and the lumens of said splines, a distal end portion of each said signal wire being deformed and extending through an opening in the outer wall of its corresponding tubing, said deformed portion being ohmically connected to one of said rings by mechanical engagement thereto;

at least one steering wire having a first end affixed to said steering actuator and extending therefrom through said central member, a second end of said at least one steering wire being affixed to the distal end of said central member;

said central member further including a first tube having its proximal end affixed to said handle, a coil spring having a proximal end attached to the distal end of said central member, and second and third tubes having their proximal ends affixed to the distal end of said coil spring, wherein said steering wire extends through said first, second and third tubes;

whereby movement of said slider means in a first direction causes contraction of said distal portion of said catheter body resulting in deployment of said lengths of multi-lumened tubing away from central member, and whereby manipulation of said steering actuator causes retraction or extension of said at least one steering wire resulting in deformation of said deformable end portion and said probe assembly thereby enabling said catheter to be steered.

9. A steerable diagnostic catheter as recited in claim 8 wherein said deformable end portion of said central member is formed by a tube including first and second lumens extending along the length thereof and having first and second coil springs disposed therein, the proximal ends of said first and second coil springs respectively engaging the distal ends of said first and second tubes, said steering wire passing therethrough, said first and second coil springs aiding in compression control of said probe assembly.

10. A steerable diagnostic catheter as recited in claim 9 wherein said probe assembly further includes a C-shaped tube having one end engaging the distal end of said first coil spring and the other end engaging the distal end of said second coil spring, said steering wire passing through said C-shaped tube.

11. A steerable diagnostic catheter as recited in claim 9 wherein said deformable end portion of said central member has a coaxially disposed lumen of generally rectangular transverse cross section extending along its length, said transverse cross section having a first dimension substantially longer than its orthogonal dimension, said first and second lumens being disposed on opposite sides of said coaxially disposed lumen and lying in a plane orthogonal to said first dimension, said coaxially disposed lumen tending to aid in the uniplanar deflection of said probe assembly.

12. A steerable diagnostic catheter comprising:

an elongated, tubular central member having a distal end and a proximal end, said central member having a deformable end portion proximate said distal end;

a catheter body having a proximal portion and a distal portion enveloping said central member, said distal portion including a probe assembly formed by a plurality of deformable lengths of multi-lumened tubing forming splines disposed in parallel and surrounding relationship to the deformable end portion of said central member, each said length of multi-lumened tubing having a first end affixed to the distal end of said central member by an end cap, and a second end affixed to the distal end of said proximal portion of said catheter body, and a plurality of electrodes distributed along the length of each spline, said electrodes being formed by circumscribing metal rings;

a handle affixed to the proximal end of said catheter body, and including a steering actuator and a slider means for enabling relative axial movement between said proximal portion and said central member;

a plurality of signal wires extending through said handle, said proximal portion and the lumens of said splines, a distal end portion of each said signal wire being deformed and extending through an opening in the outer wall of its corresponding tubing, said deformed portion being ohmically connected to one of said rings by mechanical engagement thereto;

at least one steering wire having a first end affixed to said steering actuator and extending therefrom through said central member, a second end of said at least one steering wire being affixed to the distal end of said central member, and wherein said deformable end portion of said central member is formed by a tube including first and second lumens extending along the length thereof and wherein said steering wire has a generally D-shaped transverse cross section and extends through said central member with the flat face of the portion thereof extending through said first lumen facing the flat face of the portion thereof extending through said second lumen;

whereby movement of said slider means in a first direction causes contraction of said distal portion of said catheter body resulting in deployment of said lengths of multi-lumened tubing away from central member, and whereby manipulation of said steering actuator causes retraction or extension of said at least one steering wire resulting in deformation of said deformable end portion and said probe assembly thereby enabling said catheter to be steered.

13. A steerable diagnostic catheter as recited in claim 12 wherein said deformable end portion of said central member has a coaxially disposed lumen of oval transverse cross section and wherein said probe assembly further includes a coil spring disposed within said coaxially disposed lumen.

* * * * *